United States Patent [19]
Abood et al.

[11] Patent Number: 5,612,355
[45] Date of Patent: Mar. 18, 1997

[54] PHENYL AMIDINE LACTONES USEFUL AS PLATELET AGGREGATION INHIBITORS

[75] Inventors: Norman A. Abood, Morton Grove, Ill.; Robert E. Manning, St. Louis, Mo.; Masateru Miyano, Salem, S.C.

[73] Assignee: G. D. Searle & Co., Chicago, Ill.

[21] Appl. No.: 451,815

[22] Filed: May 26, 1995

Related U.S. Application Data

[62] Division of Ser. No. 256,707, filed as PCT/US93/05861, Jun. 23, 1993, Pat. No. 5,504,106.

[30] Foreign Application Priority Data

Jun. 23, 1993 [WO] WIPO .................... PCT/US93/05861

[51] Int. Cl.$^6$ .................... C07D 405/06; A61K 31/44
[52] U.S. Cl. .................... 514/336; 514/444; 514/460; 514/422; 546/282.1; 549/60; 549/293; 548/517
[58] Field of Search .................... 546/268; 549/60, 549/293; 548/517; 514/336, 444, 460, 422

[56] References Cited

U.S. PATENT DOCUMENTS

| | | | |
|---|---|---|---|
| 4,517,686 | 5/1985 | Ruoslahti et al. | 514/12 |
| 4,578,079 | 3/1986 | Ruoslahti et al. | 623/11 |
| 4,589,881 | 5/1986 | Pierschbacher et al. | 623/11 |
| 4,614,517 | 9/1986 | Ruoslahti et al. | 623/11 |
| 4,661,111 | 4/1987 | Ruoslahti et al. | 623/11 |
| 4,683,291 | 7/1987 | Zimmerman et al. | 530/324 |
| 4,791,102 | 12/1988 | Bernat et al. | 514/19 |
| 4,857,508 | 8/1989 | Adams et al. | 514/18 |
| 4,879,313 | 11/1989 | Tjoeng et al. | 514/616 |
| 4,977,168 | 12/1990 | Bernat et al. | 514/330 |
| 5,220,050 | 6/1993 | Bovy et al. | 514/357 |

FOREIGN PATENT DOCUMENTS

| | | | |
|---|---|---|---|
| 0275748 | 7/1988 | European Pat. Off. | C07K 7/06 |
| 0298820 | 1/1989 | European Pat. Off. | C07K 7/06 |
| 0372486 | 6/1990 | European Pat. Off. | C07C 27/14 |
| 0381033 | 8/1990 | European Pat. Off. | C07C 31/19 |
| 0410540 | 1/1991 | European Pat. Off. | C07K 7/06 |
| 0445796 | 9/1991 | European Pat. Off. | C07K 5/06 |
| 0478363 | 4/1992 | European Pat. Off. | C07D 211/22 |
| 0478328 | 4/1992 | European Pat. Off. | C07C 271/22 |
| 0478362 | 4/1992 | European Pat. Off. | C07D 211/34 |
| US92/01531 | 3/1992 | WIPO . | |

OTHER PUBLICATIONS

M. Kloczewiak et al. "Platelet Receptor Recognition site on Human Fibrinogen" *Biochemistry*, 23(8), pp. 1767–1774. Jan. 1984.

Z. Ruggeri et al. "Inhibition of platelet function with synthetic pepitides designed to be high–affinity antagonists of fibrinogen binding to platelets" *Proc. Natl. Acad. Sci., USA.* 83, pp. 5708–5712. Aug. 1986.

E. Plow et al. "The Effect of ARG–GLY–ASP–containing peptides on fibrinogen and von Willebrand factor binding to platelets" *Proc. Natl. Acad. Sci., USA.* 82, pp. 8057–8061. Dec. 12, 1985.

D. Haverstick et al. "Inhibition of Platelet Adhesion to Fibronectin, Fibrinogen, and von Willebrand Factor Substrates by a Synthetic Tetrapeptide Derived From the Cell–Binding Domain of Fibronectin", *Blood* 66(4), pp. 946–952. Oct. 1985.

E. Ruoslahti et al. "New Perspectives in Cell Adhesion: RGD and Integrins" *Science.* 23, pp. 491–497. Oct. 1987.

P. Walsmann et al. "Synthetic Inhibitors of Serine Proteinases" *Pharmazie.* 29(5), pp. 333–336. Jan. 1974.

*Primary Examiner*—Jane Fan
*Attorney, Agent, or Firm*—Joy Ann Serauskas; Roger A. Williams

[57] ABSTRACT

This invention relates to phenyl amidine alkanoic acids and lactones having the following formula

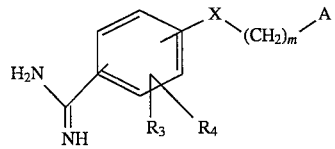

or a pharmaceutically acceptable salt which are useful in the inhibition of platelet aggregation. This invention also relates to pharmaceutical compositions of such phenyl amidine derivatives.

6 Claims, No Drawings

PHENYL AMIDINE LACTONES USEFUL AS PLATELET AGGREGATION INHIBITORS

This is a divisional application of application Ser. No. 08/256,707, filed on Jul. 21, 1994, now U.S. Pat. No. 5,504,106 issued Apr. 2, 1996 which is a 371 application of PCT/US93/05861, filed Jun. 23, 1993.

FIELD OF THE INVENTION

This invention is in the field of mammalian therapeutics and relates to compounds for the treatment of mammalian disorders such as cardiovascular disorders. Of particular interest is a class of phenyl amidines derivatives useful as inhibitors of platelet aggregation.

BACKGROUND OF THE INVENTION

Fibrinogen is a glycoprotein present as a normal component of blood plasma. It participates in platelet aggregation and fibrin formation in the blood clotting mechanism.

Platelets are cellular elements found in whole blood which also participate in blood coagulation. Fibrinogen binding to platelets is important to normal platelet function in the blood coagulation mechanism. When a blood vessel receives an injury, the platelets binding to fibrinogen will initiate aggregation and form a thrombus. Interaction of fibrinogen with platelets occurs through a membrane glycoprotein complex, known as gpIIb/IIIa; this is an important feature of the platelet function. Inhibitors of this interaction are useful in modulating platelet thrombus formation.

It is also known that another large glycoprotein named fibronectin, which is a major extracellular matrix protein, interacts with fibrinogen and fibrin, and with other structural molecules such as actin, collagen and proteoglycans. Various relatively large polypeptide fragments in the cell-binding domain of fibronectin have been found to have cell-attachment activity. See U.S. Pat. Nos. 4,517,686; 4,589,881; and 4,661,111. Certain relatively short peptide fragments from the same molecule were found to promote cell attachment to a substrate when immobilized on the substrate or to inhibit attachment when in a solubilized or suspended form. See U.S. Pat. Nos. 4,578,079 and 4,614,517.

In U.S. Pat. No. 4,683,291, inhibition of platelet function is disclosed with synthetic peptides designed to be high affinity antagonists of fibrinogen binding to platelets. U.S. Pat. No. 4,857,508 discloses tetrapeptides having utility as inhibitors of platelet aggregation.

Other synthetic peptides and their use as inhibitors of fibrinogen binding to platelets are disclosed by Koczewiak et al., *Biochem.* 23, 1767–1774 (1984); Plow et al., *Proc. Natl. Acad. Sci.* 82, 8057–8061 (1985); Ruggeri et al., *Ibid.* 83, 5708–5712 (1986); Ginsberg et al., *J. Biol. Chem.* 260 (7), 3931–3936 (1985); Haverstick et al., *Blood* 66 (4), 946–952 (1985); and Ruoslahti and Pierschbacher, *Science* 238, 491–497 (1987). Still other such inhibitory peptides are disclosed in EP Patent Applications 275,748 and 298,820.

U.S. Pat. No. 4,879,313 discloses compounds useful as inhibitors of platelet aggregation having the formula:

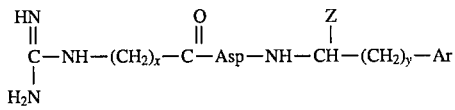

wherein
x=6 to 10,
y=0 to 4,
Z=H, COOH, $CONH_2$ OR $C_{1-6}$ alkyl,
Ar=phenyl, biphenyl or naphthyl, each substituted with 1 to 3 methoxy groups, or an unsubstituted phenyl, biphenyl, naphthyl, pyridyl or thienyl group, and
Asp=aspartic acid residue.

U.S. Pat. No. 4,977,168 discloses compounds having the following structural formula

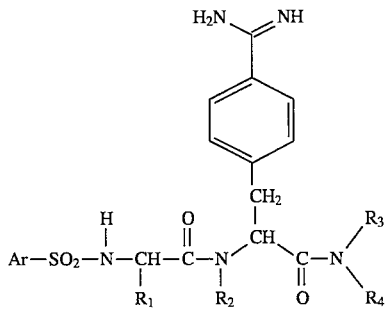

wherein $R_1$ represents hydrogen, a lower alkyl group, a lower hydroxyalkyl group, a benzyl group, a phenyl group or a 4-hydroxyphenyl group;

$R_2$ represents a lower alkyl, lower alkenyl, lower alkynyl or benzyl group, or a lower alkoxycarbonylalkyl, lower carboxyalkyl, or lower hydroxyalkyl group;

$R_3$ and $R_4$ identical or different, each represents a lower alkyl or lower hydroxyalkyl radical, lower alkenyl or lower alkynyl radical or form together with the nitrogen to which they are attached, a saturated heterocycle such as morpholino, thiomorpholino, pyrrolidino not substituted or substituted by an alkoxycarbonyl or carboxy group, piperazino, 4-(lower alkyl)piperazino, 4-(lower hydroxyalkyl)piperazino, or piperidino not substituted or substituted by one of the following groups: lower alkyl, benzyl, hydroxy, lower hydroxyalkyl, amino, lower aminoalkyl, hydroxyamino, alkoxycarbonyl or carboxy.

Ar represents a phenyl, alpha-naphthyl or beta-naphthyl group/possibly substituted, or a heteroaryl group chosen from the radicals pyridyl, quinolinyl, or isoquinolinyl, possibly substituted, as well as their isomers and their mixtures and their salts with pharmaceutically acceptable mineral or organic acids which are useful as antithrombotic agents.

U.S. Pat. No. 4,791,102 discloses compounds having the following structural formula

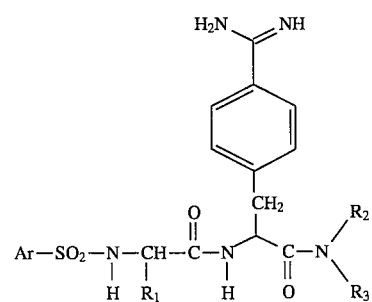

wherein
- R₁ represents a lower alkyl, lower hydroxyalkyl, or benzyl group, a phenyl or a 4-hydroxyphenyl group.
- $R_2$ and $R_3$ identical or different, each represents a lower alkyl or hydroxyalkyl, lower alkenyl or lower alkynyl radical, or they form together with the nitrogen to which they are attached, a saturated heterocycle such as morpholino, thiomorpholino, pyrrolidino unsubstituted or substituted by an alkoxycarbonyl or carboxyl group, piperazino, 4-(lower alkyl)-piperazino or piperidino unsubstituted or substituted by a lower alkyl, benzyl, hydroxy, lower hydroxyalkyl, amino, lower aminoalkyl, alkoxycarbonyl or carboxyl group.
- Ar represents a phenyl, a possibly substituted alpha-naphthyl or beta-naphthyl group, or else a heteroaryl group chosen from pyridyl, quinolinyl, isoquinolinyl, possibly substituted which are useful as selective inhibiting agents of thrombin and antithrombotics.

European Patent Application 372,486 discloses N-acyl beta amino acid derivatives of the formula:

$$R^1-CONH\text{-}(CH_2)_{0-1}\text{-}\text{[Ar]}\text{-}(CH_2)_{0-1}\text{-}CONH-\underset{R^3}{\underset{|}{CH}}-CH_2COOH$$

and their salts. Said compounds are useful for inhibiting platelet aggregation in the treatment of thrombosis, stroke, myocardial infarction, inflammation and arteriosclerosis, and for inhibiting metastasis.

European Patent Application 381 033 A1 discloses amidino or guanidino-aryl substituted alkanoic acid derivatives having the following structural formula $$R^1-A-(W)_a-X-(CH_2)_b-(Y)-B-Z-COOR$$

which are useful for the treatment of thrombosis, apoplexy, cardiac infarction, inflammation, arteriosclerosis and tumors.

European Patent Application 445,796 A2 discloses acetic acid derivatives having the formula $$H_2N(NH)C-X-Y-CO-Z-CH(Q^1)COOQ^2 \quad \text{(Formula A)}$$

where
- $Q^1$ stands for hydrogen, methyl or phenyl,
- $Q^2$ stands for hydrogen, phenyl-low-alkyl or low alkyl that can be cleaved under physiological conditions,
- X stands for 1,4-phenylene, 2,5- or 3,6-pyridylene or, 1,4-piperidinylene, which is bonded to group Y through the C atom in the 4-position,
- Y is a group having the formula $$-(CH_2)_{0-2}-CONHCH(Q^3)(CH_2)_{1-3} \quad (Y^1)$$

$$-CONHCH_3CH(Q^4) \quad (Y^2)$$

$$-(CH_2)_3NHCOCH_2- \quad (Y^3)$$

$$-NHCO(CH_2)_3- \quad (Y^4)$$

$$-(CH_2)_{0-2}-\underset{\parallel}{\overset{O}{C}}N\text{-cyclohexyl} \quad (Y^5)$$

$$\underset{\parallel}{\overset{O}{C}}N\text{-pyrrolidinyl (R)} \quad (Y^6)$$

OR $$\underset{\parallel}{\overset{O}{C}}N\text{-pyrrolidinyl (S)}\text{-}CH_2 \quad (Y^7)$$

where
- $Q^3$ stands for hydrogen, methyl, phenyl, —COOH, —COO— low-alkyl, —CONH(CH₂)₂—COOH or —CONH(CH₂)₂—COO—low-alkyl,
- $Q^4$ hydrogen, methyl or phenyl,
- Z a 1,4-piperazinylene group, a 1,4-piperazinylene group which is bonded to the CO group through the N atom in the 1-position or a group having the formula $$-NHCH(R^1)- \text{ or } -NHCH(COR^2)-$$

where
- $R^1$ stands for hydrogen, methyl, phenyl or a —COO— low-alkyl,
- $R^2$ stands for the residue of an α-aminocarboxylic acid bonded through the amino group or of an ester or amide thereof, or a group having the formula —NHCH₂CH₂—Ar, or —CO—R², or, if applicable, a mono- or di-low-alkylated carbamoyl group or a pyrrolidinoyl or piperidinoyl group,
- Ar stands for a phenyl or a phenyl substituted by low alkyl, low alkoxy, —COOH, —COO—low-alkyl, —O(CH₂)₁₋₄—COOH, —O(CH₂)₁₋₄—COO—low-alkyl, —CONH₂, —CONH—low-alkyl, —CON(low alkyl)₂, pyrrolidinoyl or piperidinoyl which are said to have inhibitory action on the bonding of adhesive proteins to blood platelets as well as blood platelet aggregation and cell-cell adhesion.

Pharmazie 29, H.5 (1974) Walsmann, et al., "Synthetische Inhibitoren von Serinproteinasen" disclosed amidinophenylalkyl/alkenylacid derivatives.

SUMMARY OF THE INVENTION

The present invention relates to a class of compounds represented by the formula $$\text{H}_2\text{N}-\underset{\parallel}{\overset{\text{NH}}{C}}-\text{[phenyl with } R_3, R_4\text{]}-X-(CH_2)_m-A$$

or a pharmaceutically acceptable salt thereof, wherein
- $R_3$ and $R^4$ are each independently selected from the group consisting of hydrogen, alkyl having 1 to 6 carbon atoms, hydroxy, alkoxy having 1 to 6 carbon atoms and halo;
- X is —CH₂CH₂—, —CH=CH—, —C≡C— or HNCO;
- m is an integer from 1 to 3; and A is the group

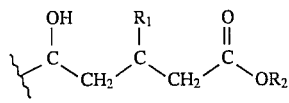

OR

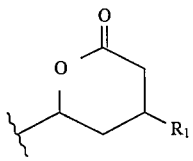

wherein

R₁ is hydrogen; hydroxy; alkyl having 1 to 6 carbon atoms; alkenyl having 2 to 6 carbon atoms which may be optionally substituted by halo; alkynyl having 2 to 6 carbon atoms; alkoxycarbonylalkyl; phenylsulfonylalkyl; alkylsulfonylalkyl; phenyl which may be optionally substituted by alkyl having 1 to 6 carbon atoms, alkoxy having 1 to 6 carbon atoms and hydroxy; a fully unsaturated heteromonocyclic ring structure having 5 or 6 ring carbon atoms wherein one of the ring carbon atoms is replaced by nitrogen, oxygen or sulfur; or cycloalkyl having 3 to 6 carbon atoms; and R₂ is hydrogen or alkyl having 1 to 6 carbon atoms.

The invention further relates to pharmaceutical compositions comprising a compound of formula I. Such compounds and compositions have usefulness as inhibitors of platelet aggregation. The invention also relates to a method of inhibiting platelet aggregation in a mammal in need of such treatment.

A preferred embodiment of the present invention is a compound of the formula

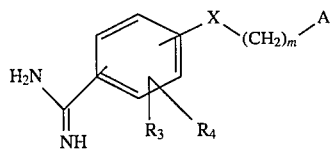

R₃ and R₄ are each independently selected from the group consisting of hydrogen, alkyl having 1 to 6 carbon atoms, hydroxy, alkoxy having 1 to 6 carbon atoms and halo;

X is —CH₂CH₂—, —CH=CH—, —C≡C— or HNCO;

m is an integer from 1 to 3; and

A is the group

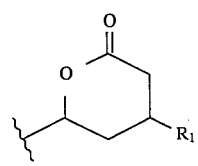

wherein

R₁ is hydrogen; hydroxy; alkyl having 1 to 6 carbon atoms; alkenyl having 2 to 6 carbon atoms which may be optionally substituted by halo; alkynyl having 2 to 6 carbon atoms; alkoxycarbonylalkyl; phenylsulfonylalkyl; alkylsulfonylalkyl; phenyl which may be optionally substituted by alkyl having 1 to 6 carbon atoms, alkoxy having 1 to 6 carbon atoms and hydroxy; a fully unsaturated heteromonocyclic ring structure having 5 or 6 ring carbon atoms wherein one of the ring carbon atoms is replaced by nitrogen, oxygen or sulfur; or cycloalkyl having 3 to 6 carbon atoms.

Exemplifying this embodiment are the following compounds:

(±)-cis-6-[4-[4-(aminoiminomethyl)phenyl]butyl]tetrahydro-4-phenyl-2H-pyran-2-one, trifluoroacetate;

(±)-cis-6-[4-[4-(aminoiminomethyl)phenyl]butyl]tetrahydro-4-hydroxy-2H-pyran-2-one, trifluoroacetate;

(±)-trans-6-[4-[4-(aminoiminomethyl)phenyl]butyl]tetrahydro-4-hydroxy-2H-pyran-2-one, trifluoroacetate;

(±)-6-[4-[4-(aminoiminomethyl)phenyl]butyl]tetrahydro-2H-pyran-2-one, trifluoroacetate;

(±)-cis-6-[4-[4-(aminoiminomethyl)phenyl]butyl]tetrahydro-4-methyl-2H-pyran-2-one, trifluoroacetate;

(±)-cis-6-[4-[4-(aminoiminomethyl)phenyl]butyl]-4-ethenyltetrahydro-2H-pyran-2-one, trifluoroacetate;

(±)-cis-methyl 2-[4-[4-(aminoiminomethyl)phenyl]butyl]tetrahydro-6-oxo-2H-pyran-4-acetate;

(±)-cis-6-[4-[4-(aminoiminomethyl)phenyl]butyl]tetrahydro-4-(3-pyridinyl)-2H-pyran-2-one, ditrifluoroacetate;

(±)-cis-6-[4-[4-(aminoiminomethyl)phenyl]butyl]tetrahydro-4-[(phenylsulfonyl)methyl]-2H-pyran-2-one, trifluoroacetate;

(±)-trans-6-[4-[4-(aminiminomethyl)phenyl]butyl]tetrahydro-4-phenyl-2H-pyran-2-one, trifluoroacetate; and N-[4-(aminoiminomethyl)phenyl]tetrahydro-6-oxo-2H-pyran-2-propanamide, trifluoroacetate.

As used herein, the term "hydrido" denotes a single hydrogen atom (H). This hydrido group may be attached, for example, to a oxygen atom to form a hydroxyl group; or, as another example, two hydrido groups may be attached to a carbon atom to form a —CH₂— group.

As used herein, the term "alkyl", either alone or within other terms such as "alkylcarboxyalkyl" embraces a linear or branched chain saturated hydrocarbon radical having 1 to 6 carbon atoms. Illustrative of such radicals are methyl, ethyl, propyl, 1-methylethyl, butyl, 2-methylpropyl, 1-methylpropyl, 1,1-dimethylethyl, pentyl, 3-methylbutyl, 1-methylbutyl, 1-ethylpropyl, 2,2-dimethylpropyl, 1,1-dimethylpropyl, hexyl, and 4-methylpentyl.

As used herein, the term "alkoxy" embraces linear or branched oxy-containing radicals each having alkyl portions of 1 to 6 carbon atoms. Illustrative of such groups are methoxy, ethoxy, propoxy, butoxy, 1-methylethoxy, 2-methylpropoxy, 1-methylpropoxy, 1,1-dimethylethoxy, pentenyloxy, 3-methylbutoxy, 1-methylbutoxy, 1-ethylpropoxy, 2-2-dimethylpropoxy, 1,1-dimethylpropoxy, hexenyloxy, and 4-methylpentoxy.

As used herein the term "alkenyl" embraces linear or branched unsaturated hydrocarbon radicals having 2 to 6 carbon atoms and containing at least one carbon to carbon double bond, which carbon to carbon double bond may have either cis or trans geometry within the alkenyl moiety. Said alkenyl moiety may be further substituted with one or more halo atoms, such as fluoro, chloro or bromo, to provide a haloalkenyl group. Illustrative of such groups are ethenyl, propenyl, butenyl, isobutenyl, pentenyl, 3-methyl-1-butenyl, 2-methyl-2-butenyl, 2,3-dimethyl-2-butenyl and hexenyl.

As used herein the term "alkynyl" embraces linear or branched unsaturated hydrocarbon radicals having 2 to 6 carbon atoms and containing one carbon to carbon triple bond. Illustrative of such radicals are ethynyl, propynyl, butynyl, pentynyl, and hexynyl.

As used herein the term "halo" embraces halogen atoms. Illustrative of such atoms are chloro (Cl), fluoro (F), bromo (Br) and iodo (I).

As used herein, the term "alkoxycarbonylalkyl" represents the radical of the formula

RCOOR wherein the R represents an alkyl group having 1 to 6 carbon atoms which may or may not be the same. Illustrative of such groups are methoxycarbonylmethyl and ethoxycarbonylmethyl.

As used herein the term "heteromonocyclic" embraces fully unsaturated, cyclic hydrocarbon radicals having 5 or 6 ring carbon atoms wherein 1 of the ring carbons is replaced by nitrogen, oxygen or sulfur. Illustrative of such radicals are pyridinyl, pyrrolyl, thiophenyl, furanyl and pyranyl. Attachment of the heteromonocyclic structure to the remaining portion of the molecule represented by formula I may be through a ring carbon atom of the heteromonocyclic structure.

As used herein the term "cycloalkyl" embraces cyclic radicals having three to six carbon atoms. Illustrative of such groups are cyclopropyl, cyclobutyl, cyclopentyl and cyclohexyl.

As used herein the term "phenyl" denotes a monocyclic arene in which one hydrogen atom from a carbon atom of the ring has been removed.

Substitution to said phenyl radical can be to any available ring carbon atom.

As the compounds of the present invention may contain one or more asymmetric carbon atoms, the invention includes all of the possible enantiomeric and diastereomeric forms of the compounds of formula I. The compounds of Formula I which contain two centers of asymmetry may produce four possible stereoisomers designated as the RR, RS, SR and SS enantiomers; all four stereoisomers are considered within the scope of this invention. As used herein and in the claims the prefix (±) is used to specify the racemic nature of a particular compound.

The term "phenylsulfonylalkyl" refers to the compound having the following structure

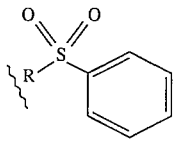

wherein R represents an alkyl group having 1 to 6 carbon atoms.

The term "alkylsulfonylalkyl" refers to the compound having the following structure

—RSO$_2$R wherein R represents an alkyl group having 1 to 6 carbon atoms.

Tautomeric forms are also included as well as pharmaceutically acceptable salts of such isomers and tautomers.

Compounds of formula I wherein A is 2H-pyran-2-onyl may under physiological conditions open to give the open-chain acids and corresponding salts. All such open-chain salts are meant to be included within the present invention.

In the structures and formulas herein, the bond drawn across a bond of an aromatic ring can be to any available atom on the aromatic ring.

The term "pharmaceutically acceptable salt" refers to a salt prepared by contacting a compound of formula (I) with an acid whose anion is generally considered suitable for human consumption. Examples of pharmacologically acceptable salts include the hydrochloride, hydrobromide, hydroiodide, sulfate, phosphate, acetate, propionate, lactate, maleate, malate, succinate, and tartrate salts. All of these salts may be prepared by conventional means by reacting, for example, the appropriate acid with the corresponding compound of Formula I.

The compounds of formula I were prepared in a conventional manner using standard synthetic methods. In general, these benzamidine/lactones were prepared from the benzonitrile 2 (scheme A), by a three step procedure: 1) H$_2$S treatment to form the thioamide, 2) alkylation with iodomethane leading to the thioimidate and 3) treatment of the thioimidate with ammonium acetate.

The lactone portion of the molecule was prepared by a variety of methods depending on the particular ring substituent R as outlined in schemes B, C and D. The synthesis of hydroxylactones 6 and 7 and intermediates 3 and 8 are outlined in scheme B. Thus the halobenzonitrile was coupled to an omega alkynol via a palladium mediated coupling reaction employing tetrakis(triphenylphosphine) palladium (0) [for related conditions see: H. A. Dieck and F. R. Heck, *J. Organometallic Chem.* 259–263(1975)]. Compounds where X=CH$_2$CH$_2$ were prepared by a selective hydrogenation using palladium on calcium carbonate. Swern oxidation provided the aldehyde intermediate 3. Treatment of 3 with the dianion of methyl acetoacetate followed by sodium borohydride reduction gave a mixture of anti and syn diol esters (4a,5a) which were separated by column chromatography. Alternatively, reduction with tetramethylammonium triacetoxyborohydride afforded 4a selectively [cf. D. A. Evans, K. T. Chapman and E. M. Carreira, *J. Am. Chem. Soc.* 110, 360–78 (1988)]. Saponification afforded the corresponding dihydroxy acid diastereomers 4b and 5b which were converted to the target compounds according to scheme A as either the zwitterionic amidine/acid or amidine/lactone depending on the workup procedure (see examples). Finally, lactonization (TFA/1,2-dichloroethane) of 4b and β-elimination of 6 (MsCl/Et$_3$N) gave the unsaturated lactone intermediate 8.

Scheme C outlines the general methods used to synthesize a variety of substituted lactones. Stereoselective 1,4-addition (method 1) of vinyl cuprate to 8 [cf. W. H. Pirkle and P. E. Adams *J. Org. Chem.* 45, 4117–21 (1980)] followed by saponification and treatment of the crude hydroxy acid with triphenylphosphine and diethylazodicarboxylate (DEAD) [cf. 0. Mitsunobu *Synthesis* 1–28 (1981)] gave the cis lactone 9. The final target compound was synthesized according to the protocol in scheme A.

Conjugate addition of methyl phenylsulphonylacetate to 8 (method 2) gave the trans lactone intermediate 10 which underwent isomerization to the cis lactone 11 under the desulfonylation condition of sodium amalgam in methanol [cf. J. A. Marshal, R. C. Andrews and L. Lebioda *J. Org. Chem.* 52, 2378–88 (1987)]. Phenylsulfone 12 was prepared from 10 via dealkylative decarboxylation with sodium chloride in wet DMSO [cf. A. P. Krapcho *Synthesis* 893–914 (1982)] followed by saponification and Mitsunobu inversion. Additionally, trans aryl compounds (e.g. 13) were synthesized via aryl cuprate addition to 8 (method 3). Elaboration to the final target compound was carried out as outlined in scheme A.

Methods 4, 5 and 6 utilize the intermediate aldehyde 3. Aldol condensation (method 4) of 3 with the lithium enolate of acetophenone afforded a β-hydroxy ketone. Esterification with bromoacetyl bromide/pyridine followed by samarium iodide induced cyclization of the bromoester afforded the lactone 14 as a single diastereoisomer [cf. G. A. Molander and J. B. Etter, *J. Am. Chem. Soc.* 109, 6556–58 (1987)]. Dehydration with thionyl chloride/pyridine followed by selective hydrogenation using palladium on calcium carbonate gave the cis phenyl lactone 15.

Method 5 outlines the synthesis of methyl lactone 19. Treatment of the aldehyde 3 with an in situ generated methallylzinc reagent [cf. T. Shono, M. Ishifune and S. Kashimura *Chemistry Letters* 449–52 (1990)] afforded the homoallylic alcohol 16. Ozonolysis, acylation and samarium iodide induced cyclization provided the lactone 17 as a single diastereomer. At this stage the benzonitrile was converted to the benzamidine 18 by the sequence outlined in scheme A. Elimination under acidic conditions (trifluoroacetic anhydride/trifluoroacetic acid) followed by hydrogenation of the unsaturated lactone with 10% palladium on carbon afforded the cis methyl lactone 19.

Method 6 is a variation on method 3 featuring an intramolecular Wittig-Horner reaction [cf. G. R. Weihe and T. C. McMorris *J. Org. Chem.* 43, 3942(1978)] in order to append a pyridyl moiety on the lactone ring. Aldol condensation affords the β-hydroxy ketone 20. Acylation with dimethylphosphonoacetyl chloride/pyridine followed by treatment with sodium hydride provided the unsaturated lactone 21. Catalytic hydrogenation (5% Pd/C) gave a cis lactone, which when treated with excess lithium bis(trimethylsilyl)amide followed by acidic workup afforded the target benzamidine 22 directly [cf. R. T. Boere, R. T. Oakley and R. W. Reed, *J. Organometallic Chem.* 161–7 (1987)].

Scheme D outlines the method used for compounds of formula 1 where X=HNCO. Known lactone 23 [cf. A. Ijima, H. Mizuno and K. Takahashi *Chem. Pharm. Bull.* 19, 1053–5 (1971)] was oxidized to the carboxylic acid (NaIO₄/RuCl₃), converted to the acid chloride [(COCl)₂/DMF (cat.)] and coupled directly with 4-aminobenzonitrile affording the intermediate 24. Synthesis of the benzamidine according to the procedure outlined in scheme A yielded the desired target compounds.

Scheme E illustrates the synthesis of the chiral hydroxylactone 29 by combining some synthetic concepts outlined in schemes B and D. The known hydroxy ester (25), synthesized in 98% e.e., [D.F. Taber, L. J. Silverberg *Tetrahedron Letters* 32, 4227–4230 (1991)] underwent a Claisen condensation with excess lithio t-butyl acetate. Stereoselective reduction of the hydroxyketoester 26 with tetramethylammonium triacetoxyborohydride gave the anti diol ester Hydrolysis, lactonization and silyl protection gave the lactone 28 in high yield. Oxidative cleavage of the trisubstituted olefin and activation of the resulting carboxylic acid to the acid chloride under neutral conditions [S. E. Kelly, T. G. LaCour *Synthetic Comm.* 22, 859–869 (1992).] followed by coupling with aminobenzamidine dihydrochloride gave the penultimate product. Removal of the silyl protecting group using aq. HF in acetonitrile afforded the desired lactone 29.

Scheme A

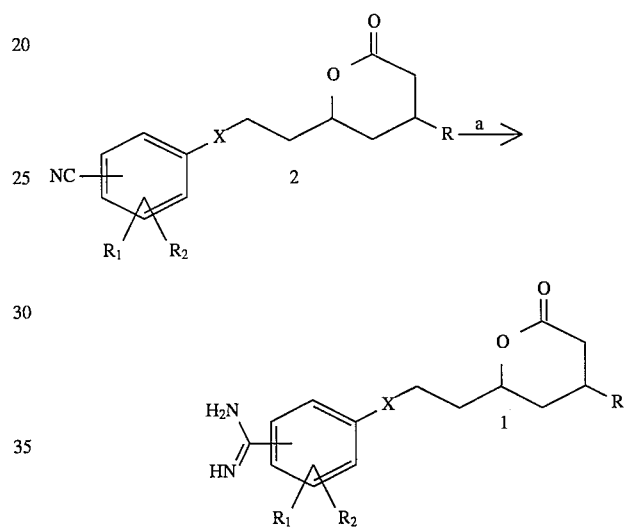

ᵃ1) H₂S; 2) CH₃I; 3) NH₄OAc

Scheme B

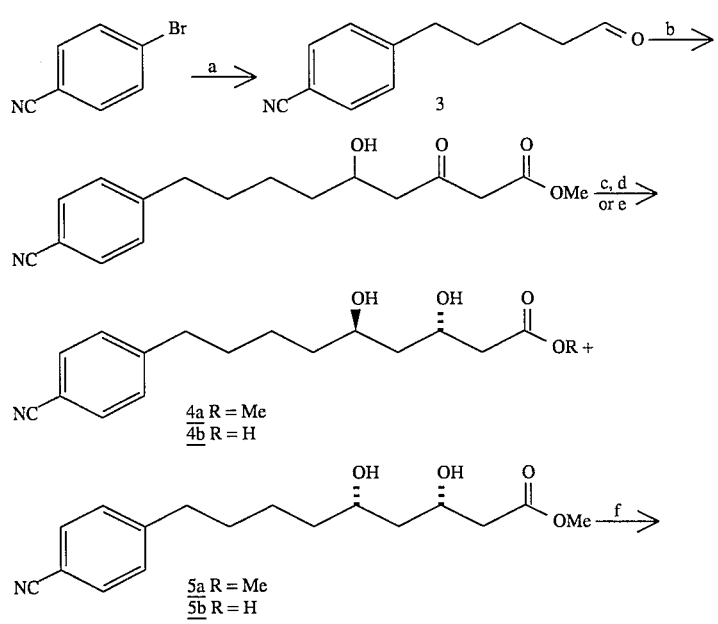

-continued
Scheme B
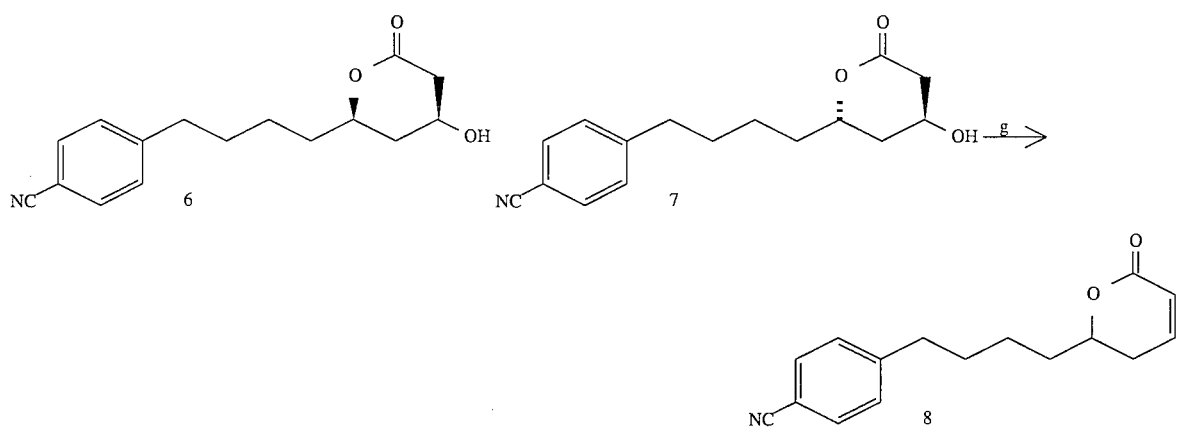
<sup>a</sup>1) Pd(Ph₃P)₄, 4-pentyn-1-ol; 2) H₂, 5% Pd/CaCO₃ (optional); 3) (COCl)₂, DMSO, Et₃N;
<sup>b</sup>Methyl acetoacetate, NaH, nBuLi;
<sup>c</sup>1) NaBH₄; 2) separate;
<sup>d</sup>1) aq. NaOH;
<sup>e</sup>Me₄NBH(OAc)₃;
<sup>g</sup>TFA, ClCH₂CH₂Cl;
<sup>g</sup>MsCl, Et₃N.
Scheme C
Method 1
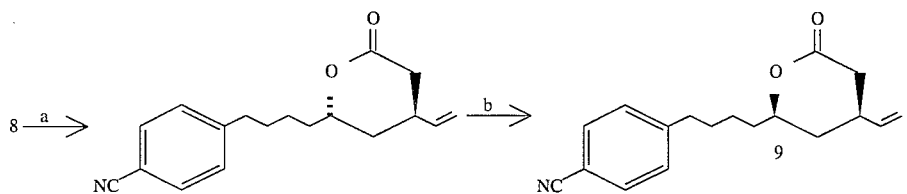
Method 2
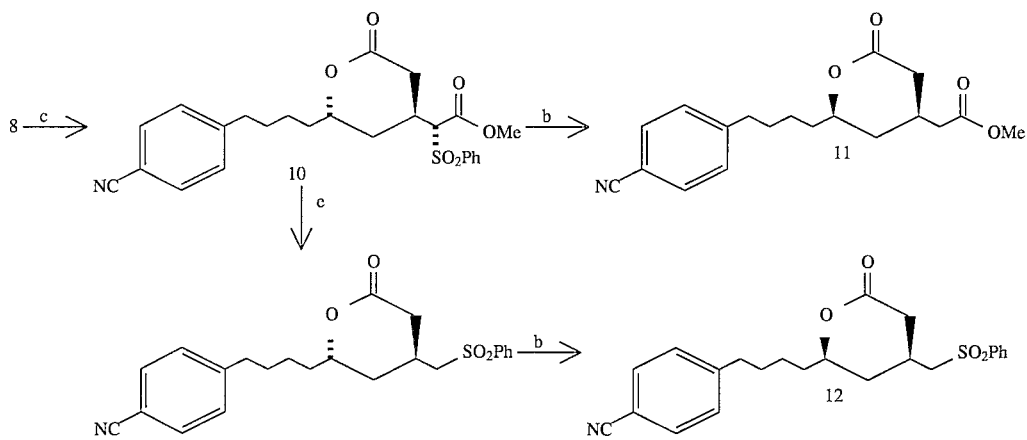
Method 3
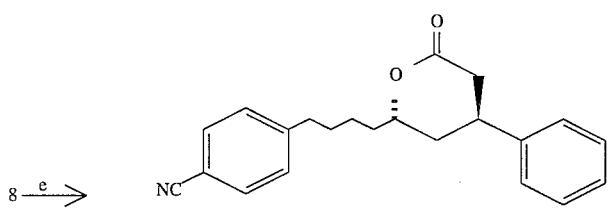
<sup>a</sup>(vinyl)₂CuCNLi₂;

-continued
Scheme C
b 1) aq. NaOH; 2) Ph₃P, DEAD;
c methyl phenylsulfonylacetate, KOtBu; d Na(Hg); e NaCl, wet DMSO; e Ph₂CuCNLi₂.
Method 4
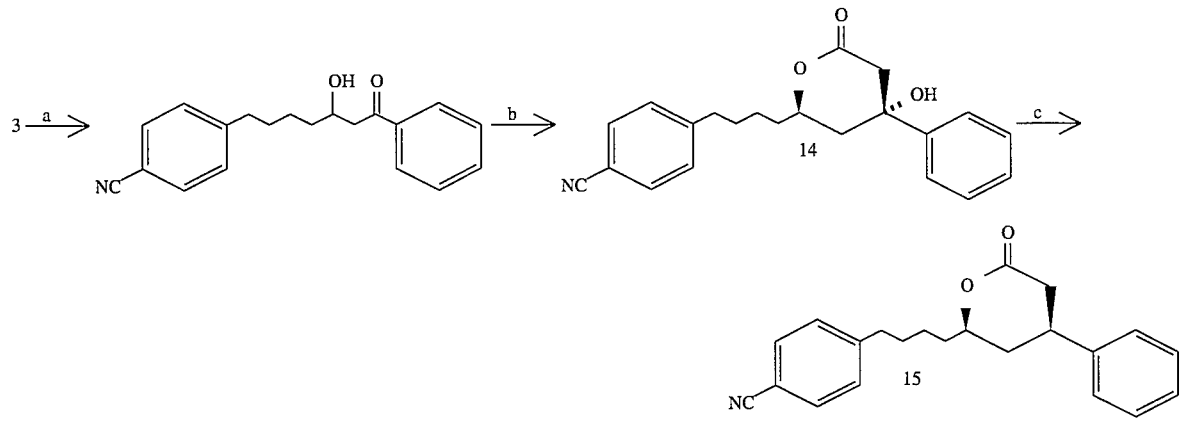
Method 5
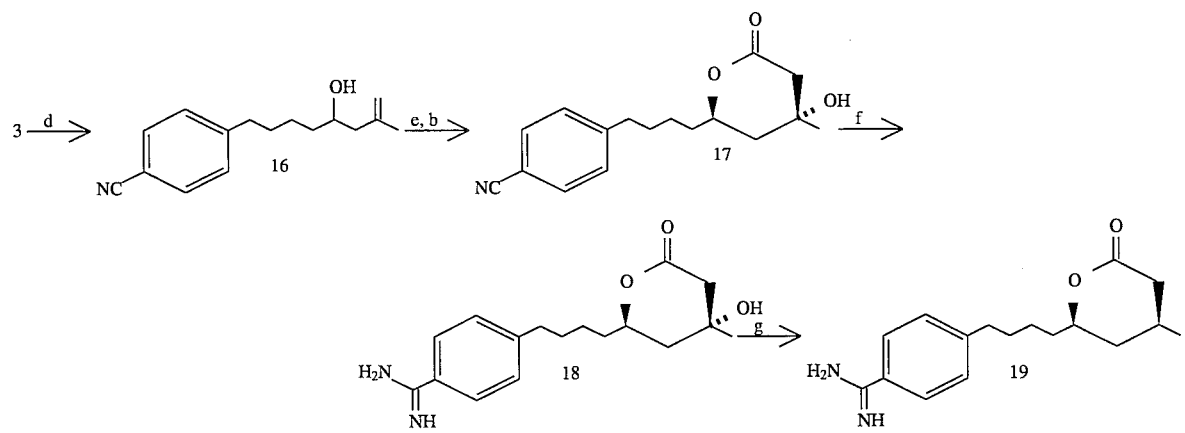
a acetophenone, LDA;
b 1) bromoacetyl bromide, pyridine; 2) SmI₂;
c 1) SOCl₂, pyridine; 2) H₂, 5% Pd/CaCO₃;
d methallyl chloride, NaI, Zn;
e O₃, dimethylsulfide;
f 1) H₂S; 2) MeI; 3) NH₄OAc;
g 1) TFA, TFAA; 2) H₂, 10% Pd/C.
Method 6
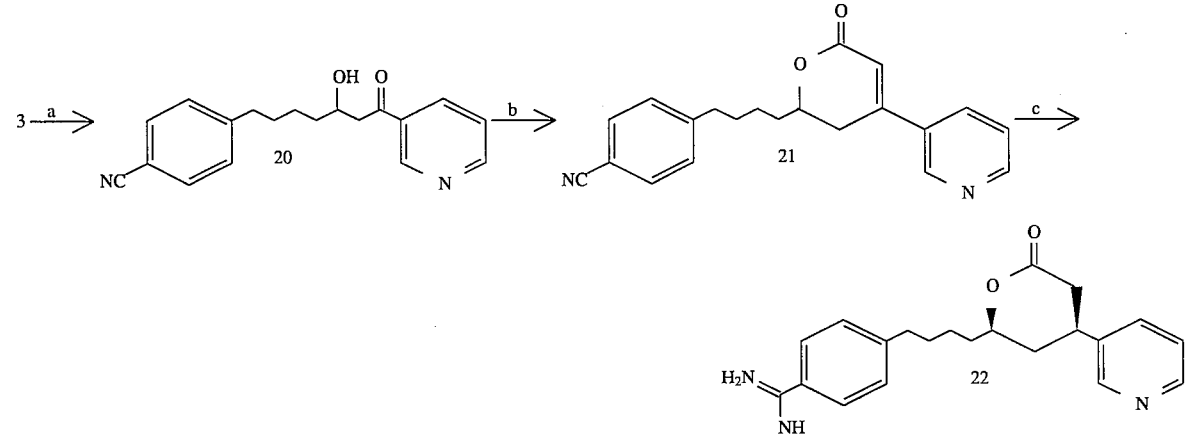

[a]3-acetylpyridine, LDA;
[b]1) P,P-dimethylphosphonoacetyl chloride, pyridine; 2) NaH;
[c]1) H₂, 5% Pd/C; 2) LiN(SiMe₃)₂; 3) aq. HCl.

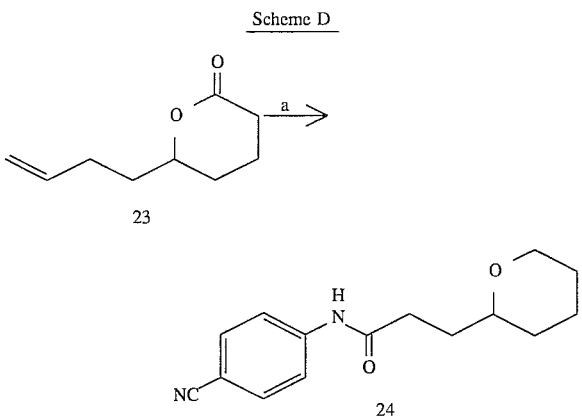

[a]1) NaIO₄, RuCl₃; 2) (COCl)₂ then 4-aminobenzonitrile, Et₃N

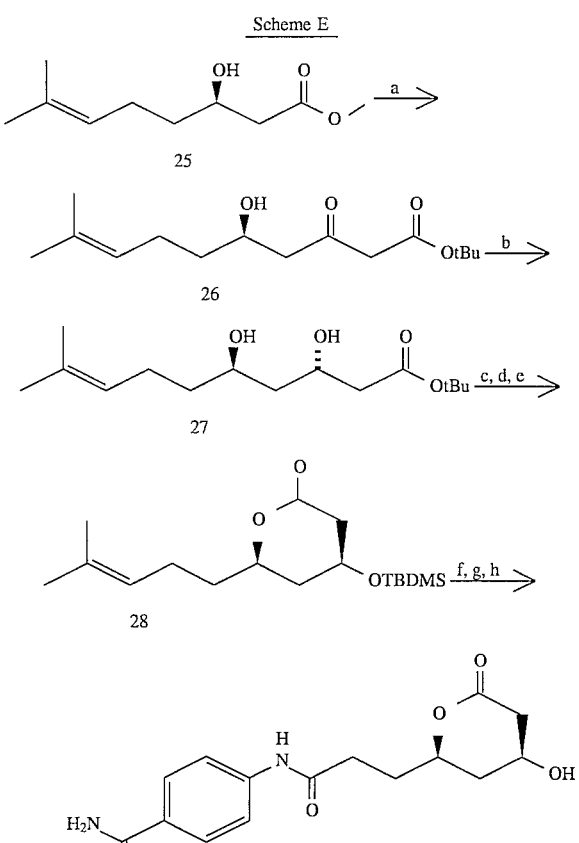

[a]LiHMDS, tBuOAc;
[b]Me₄NBH(OAc)₃;
[c]aq. NaOH;
[d]benzene, reflux;
[e]TBDMSCl, Imidazole;
[f]RuCl₃, NaIO₄;
[g]1) TMSCl, pyridine 2) (COCl)₂ 3) aminobenzamidine dihydrochloride;
[h]aq. HF/acetonitrile.

This invention also relates to a method of inhibiting platelet aggregation and more specifically, a method of treatment involving the administration of compounds of Formula I to achieve such inhibition.

For the inhibition of platelet aggregation compounds of Formula I may be administered orally, parenterally, or by inhalation spray or rectally in dosage unit formulations containing conventional non-toxic pharmaceutically acceptable carriers, adjuvants and vehicles. The term parenteral as used herein includes, for example, subcutaneous, intravenous, intramuscular, intrasternal, infusion techniques or intraperitonally.

The compounds of the present invention may be administered by any suitable route, preferably in the form of a pharmaceutical composition adapted to such a route, and in a dose effective for the treatment intended. Therapeutically effective doses of the compounds of the present invention required to prevent or arrest the progress of the medical condition are readily ascertained by one of ordinary skill in the art.

Accordingly, the invention provides a class of novel pharmaceutical compositions comprising one or more compounds of the present invention in association with one or more non-toxic, pharmaceutically acceptable carriers and/or diluents and/or adjuvants (collectively referred to herein as "carrier" materials) and if desired other active ingredients.

The dosage regimen for treating a condition with the compounds and/or compositions of this invention is based on a variety of factors, including the type, age, weight, sex and medical condition of the patient; the severity of the condition; the route of administration; and the particular compound employed. Thus dosage regimen may vary widely. Dosage levels of the order from about 0.01 mg to about 150 mg per kilogram of body weight per day are useful in the treatment of the above-indicated conditions (from about 10 mg to about 10500 mg per patient per day). For oral administration a daily dose of from about 0.01 to 150 mg/Kg body weight, particularly from about 1 to 30 mg/Kg body weight may be appropriate. For administration by injection a preferred daily dose would be from about 0.01 to 50 mg/Kg body weight.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. These may contain, for example, an amount of active ingredient from about 1 to 250 mg, preferably from about 25 to 150 mg. A suitable daily dose for a mammal may vary widely depending on the condition of the patient and other factors.

The active ingredient may also be administered by injection as a composition wherein, for example, saline, dextrose or water may be used as a suitable carrier. A suitable daily dose would typically be about 0.01 to 50 mg/kg body weight injected per day in multiple doses depending on the condition being treated.

For administration the compounds of this invention are ordinarily combined with one or more adjuvants appropriate to the indicated route of administration. The compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulphuric acids, gelatin, acacia, sodium alginate, polyvinylpyrrolidone, and/or polyvinyl alcohol, and tableted or encapsulated for convenient administration. Alternatively, the compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

The pharmaceutical compositions may be made up in a solid form such as granules, powders or suppositories or in a liquid form such as solutions, suspensions or emulsions. The pharmaceutical compositions may be subjected to conventional pharmaceutical operations such as sterilization and/or may contain conventional pharmaceutical adjuvants such as preservatives, stabilizers, wetting agents, emulsifiers, buffers, etc.

The following Examples are intended to further illustrate the present invention and not to limit the invention in spirit or scope. In the Examples temperature is in degrees Celsius unless otherwise expressly set forth.

EXAMPLE 1

Preparation of (±)-4-(Aminoiminomethyl)-βS, δR-dihydroxybenzenenonanoic acid and (±)-cis-6-[4-[4-Aminoiminomethyl)phenyl]butyl]tetrahydro-4-hydroxy-2H-pyran-2-one, trifluoroacetate

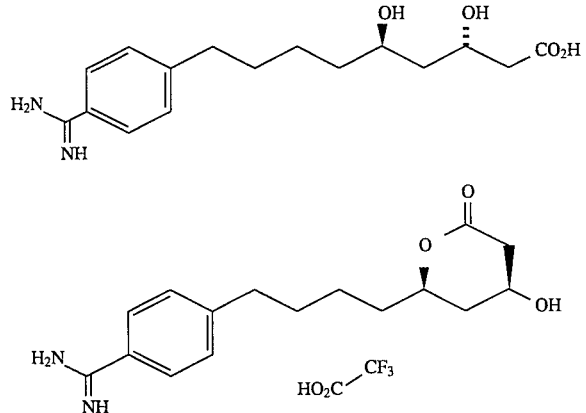

A. Preparation of 5-(4-cyanophenyl)-4-pentynol

To a solution of 4-bromobenzonitrile (105.0 g, 0.577 mol) and triethylamine (108.1 g, 1.07 mol) in 900 mL of acetonitrile under nitrogen was added 4-pentynol (50.0 g, 0.594 mol) dissolved in acetonitrile followed by tetrakis(triphenylphosphine)palladium(0) (5.00 g, 3.23 mmol). The reaction flask was wrapped in aluminum foil and the mixture was refluxed for 20 hours, cooled to room temperature and filtered. The filtercake was washed with acetonitrile and the filtrate was evaporated under reduced pressure. The residue was dissolved in EtOAc and washed successively with water, aq. HCl, water, 5% aq. $K_2CO_3$, water, and brine. The organic layer was dried ($MgSO_4$) and the solvent removed under reduced pressure. The residue was dissolved in 1.8 L of diethyl ether, treated with charcoal, filtered and the filtrate reduced to a volume of 550 mL on a steam bath. A solid yellow precipitate formed upon cooling to −30° C. The solid was filtered and washed with cold diethyl ether and dried affording 72.90 g of the title product (m.p. 76.83° C.). The filtrate was concentrated under reduced pressure and chromatographed (EtOAc: hexane, 1:1) affording 10.2 g of title product after recrystallization from diethyl ether (m.p. 81°–84° C., 78% combined yield).

Anal. calc'd. for $C_{12}H_{11}NO$: C, 77.82; H, 5.99; N, 7.56. Found: C, 77.30; H, 6.08; N, 7.38.

B. Preparation of 5-(4-cyanophenyl)pentanol

To a solution of the product of step A (65.0 g, 0,351 mol) in methanol (1 L) was added 5% $Pd/CaCO_3$ (6.50 g) and hydrogenated at 5 psi for 3.5 hours. The catalyst was removed and the solvent evaporated under reduced pressure. The light brown residue was dissolved in $CH_2Cl_2$ (150 mL) and passed through a bed of silica gel and eluted with $CH_2Cl_2$. The solvent was removed under reduced pressure yielding 55.6 g (84%) of the title product which solidified on standing (m.p. 39°–41° C.).

Anal. calc'd. for $C_{12}H_{15}NO$: C, 76.16; H, 7.99; N, 7.40. Found: C, 76.09; H, 7.93; N, 7.28.

C. Preparation of 5-(4-cyanophenyl)pentanal

A solution of DMSO (9.36 g, 120 mmol) in 20 mL of $CH_2Cl_2$ was added dropwise over 10 minutes to a solution of oxalyl chloride (10.16 g, 80 mmol) in $CH_2Cl_2$ (80 mL) at −70° C. under an atmosphere of nitrogen. After stirring for 15 minutes at −70° C., a solution of the product of step B (7.56 g, 40.0 mmol) in $CH_2Cl_2$ (50 mL) was added dropwise over 10 minutes and the solution was stirred at −70° C. for 15 minutes. Neat triethylamine (24.2 g, 240 mmol) was added rapidly, the ice bath was removed and the mixture allowed to warm to ambient temperature over 30 minutes. The reaction mixture was diluted with $CH_2Cl_2$ (100 mL), washed successively with water, 1N $NaHSO_4$ and brine, dried ($MgSO_4$), filtered through a pad of silica gel and eluted with $CH_2Cl_2$. The solvent was evaporated under reduced pressure affording 7.23 g of title product (97%) as a thick oil of sufficient purity to be used in the next reaction. $^1$H-NMR (300 MHz, $CDCl_3$) 61.67 (m, 4H), 2.47 (m, 2H), 2.70 (m, 2H), 7.37 (d, J=8HZ, 2H), 7.48 (d, J=8Hz, 2H), 9.77 (s, 1H).

D. Preparation of methyl 9-4-cyanophenyl)-3,5-dihydroxynonanoate

Neat methyl acetoacetate (2.33 g, 20 mmol) was added dropwise to a suspension of NaH (60% oil suspension) (800 mg, 20.0 mmol) in dry THF (40 mL) at 0° C. under a nitrogen atmosphere. The resulting solution was stirred at 0° C. for 15 minutes and treated with a 1.6M solution (12.5 mL, 20 mmol) of n-BuLi in hexane added dropwise over 5 minutes. The yellow solution was stirred at 0° C. for 15 minutes whereupon the product of step C (3.74 g, 20 mmol) in THF (10 mL) was added via canula and stirred at 0° C. for 30 minutes. The reaction mixture was poured into 1N $NaHSO_4$ (100 mL) and extracted with ETOAc, dried ($MgSO_4$), filtered and evaporated under reduced pressure. The crude hydroxyketo ester was dissolved in methanol (50 mL) and cooled to −30° C. Solid $NaBH_4$ (760 mg, 20 mmol) was added and the reaction was stirred at −30° C. for 2 hours, poured into 1N $NaHSO_4$, extracted with EtOAc, dried ($MgSO_4$), filtered and concentrated under reduced pressure. Silica gel chromatography (EtOAc:toluene, 4:6) afforded two diastereomeric diol esters.

Diastereomer A (610 mg) solidified to a waxy solid on standing.

Anal. calc'd. for $C_{17}H_{23}NO_4$: C, 66.86; H, 7.59; N, 4.59. Found: C, 66.16; H, 7.74; N, 4.35.

$^1$H-NMR (300 MHz, $CDCl_3/D_2O$) 61.25–1.75 (m, 8H), 2.50 (d, J=6 Hz, 2H), 2.68 (t, J=7 Hz, 2H), 3.72 (s, 3H), 3.86 (m, 1H), 4.26 (pent., J=7 Hz, 1H), 7.27 (d, J=8 Hz, 2H), 7.57 (d, J=8 Hz, 2H) .

Diastereomer B was recrystallized from methyl t-butyl ether/diisopropyl ether (1:1) affording 720 mg of product (m.p. 88.93° C.).

Anal. calc'd. for $C_{17}O_{23}NO_4$: C, 66.86; H, 7.59; N, 4.59. Found: C, 66.65; H, 7.72; N, 4.51.

$^1$H-NMR (300 MHz, CDCl$_3$/D$_2$O) 61.3–1.7 (m, 8H), 2.47 (dd, J=5 Hz, J=12 Hz, 1H), 2.55 (dd, J=7 Hz, J=12Hz, 1H), 2.68 (t, J=7Hz, 2H), 3.72 (s, 3H), 3.90 (m, 1H), 4.34 (m, J=5 Hz, 1H), 7.27 (d, J=8 Hz, 2H), 7.57 (d, J=8 Hz, 2H).

The syn/anti assignment of the two diol diastereomers was determined by NMR analysis of the corresponding lactones as compared to the literature [for NMR analysis of related compounds see: W. F. Hoffman, et al. *J. Med. Chem.* 29, 159–169 (1986)] and is described below.

E. Preparation of trans-6-[4-Cyanophenyl)butyl]3,4,5,6-tetrahydro-4-hydroxy-2H-pyran-2-one To a solution of diasteriomer A, step D (55 mg, 0.180 mmol) in THF (3 mL) was added 1N aq. NaOH (200 uL, 0.20 mmol) and the solution stirred at room temperature for 30 minutes. The reaction mixture was acidified by adding 2N HCl (200 uL), stirred for 5 minutes, treated with MgSO$_4$, filtered and concentrated under reduced pressure. The residue was taken up in 1,2-dichloroethane (5 mL). Trifluoroacetic acid (20 uL, 0.26 mmol) was added and the solution stirred at 50° C. for 1 hour. Removal of the solvent under reduced pressure gave 50 mg of product as a colorless oil.

$^1$H-NMR (300 MHz, CDCl$_3$) δ 1.30–1.80 (m, 7H), 1.90–2.00 (m, 1 H), 2.40–2.60 (m, 4H), 4.40 (m, 1H), 4.70 (m, 1H), 7.27 (d, J=8 Hz, 2H), 7.57 (d, J=8 Hz, 2H).

F. Preparation of cis-6-[4-(4-Cyanophenyl)butyl]-3,4,5,6-tetrahydro-4-hydroxy-2H-pyran-2-one The title compound was synthesized from diasteriomer B, step D (55 mg, 0.180 mmol) in a manner similar to step E affording 50 mg of a colorless oil.

$^1$H-NMR (300 MHz, CDCl$_3$) δ 1.40–1.80 (m, 7H), 2.19–2.30 (m, 1H), 2.48 (dd, J=8 Hz, J=16 Hz, 1H), 2.78 (t, J=7 Hz, 2H), 2.91 (dd, J=6 Hz, J=16 Hz, 1H), 4.15–4.32 (m, 2H), 7.27 (d, J=8 Hz, 2H), 7.57 (d, J=8 Hz, 2H).

The stereochemical assignment was based on the observation that the axial hydroxyl group in the lactone of diastereomer A deshields the C-6 lactone proton (δ 4.70) by 0.47 ppm compared to the chemical shift assignment of the corresponding proton on the lactone diastereomer B (δ~4.2) (see W. F. Hoffman, et al., 1986). Additional supporting evidence was obtained when the hydroxy-keto ester intermediate in step D was stereoselectively reduced with tetramethylammonium triacetoxyborohydride [cf. D. A. Evans, K. T. Chapman and E. M. Carreira *J. Am. Chem. Soc.* 110, 3560–78 (1988)] to give the anti diol ester whose NMR spectrum was identical in every respect to diastereomer B in step D.

G. Preparation of (±)-4-(Aminoiminomethyl)-βS, R-dihydroxybenzenenonanoic acid and (±)-cis-6-[(4-(4-(aminoiminomethyl)phenyl)butyl]-3,4,5,6-tetrahydro-4-hydroxy-2H-pyran-2-one To a solution of diasteriomer B, step D (392 mg, 1.29 mmol) in MeOH (10 mL) was added aq. 1N NaOH (1.9 mL, 1.9 mmol) and the solution stirred at room temperature for 1 hour. The reaction was poured into 1N NaHSO$_4$, extracted with EtOAc, dried (MgSO$_4$) and evaporated under reduced pressure. To the crude dihydroxy acid in pyridine (10 mL) was added triethylamine (781 mg, 7.74 mmol). Hydrogen sulfide gas was bubbled through the solution for 5 minutes at room temperature, then stoppered and stirred at room temperature for 2 days. The solvent was removed under reduced pressure and the yellow residue partitioned between EtOAc and 1N NaHSO$_4$. The organic layer was dried (MgSO$_4$), filtered and evaporated under reduced pressure. To the resulting thioamide in acetone (10 mL) was added iodomethane (1.83 g, 12.90 mmol) and the reaction stirred at 55° C. under an atmosphere of nitrogen for 35 minutes. Removal of the solvent under reduced pressure afforded the crude thioimidate HI. To this yellow residue was added anhydrous ammonium acetate (198 mg, 2.58 mmol) and methanol (10 mL). The solution was stirred at 55° C. for 3.5 hours under an atmosphere of nitrogen then concentrated under reduced pressure. The residue was dissolved in water (2 mL) and the product was precipitated as the zwitterion by the addition of acetone (30 mL). The precipitate was filtered and washed successively with water:acetone (1:15), acetone, acetonitrile, and diethyl ether affording 130 mg of the title compound (acid) as an off-white amorphous product (m.p. 238°–242° C.)

Anal. calc'd. for $C_{16}H_{24}N_2O_4O.4H_2O$: C, 60.55; H, 7.92; N, 8.88. Found: C, 60.92,; H, 7.70; N, 8.46.

The filtrate was evaporated under reduced pressure and purified by reverse phase chromatography on a Waters® C-18 Delta Pak column using a 0.05% TFA/water:acetonitrile gradient affording 210 mg of the title compound (lactone) as the TFA salt after dissolving the residue in hot CH$_3$CN, cooling, then precipitation with Et20 (m.p. 150°–152° C. dec.).

Anal. calc'd. for $C_{18}H_{23}N_2O_5F_3O.5H_2O$: C, 52.29; H, 5.85; N, 6.78 . Found: C, 52.16; H, 5.62; N, 6.71.

EXAMPLE 2

Preparation of (±)-trans-6-[4-[4-(Aminoiminomethyl)phenyl]butyl]tetrahydro-4-hydroxy-2H-pyran-2-one, trifluoroacetate

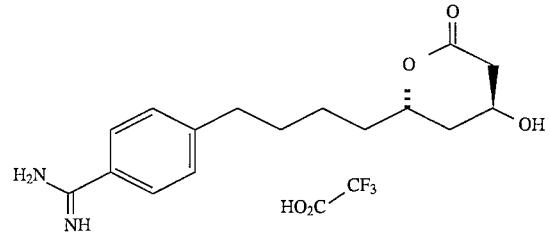

The title compound was prepared from the product of example 1, step D (diasteriomer A, 350 mg, 1.15 mmol) in a manner similar to example 1, step G affording 115 mg (25%) of lactone product as the TFA salt after reverse phase chromatography (m.p. 159°–160° C.).

Anal. calc'd. for $C_{18}H_{23}N_2O_5F_3 0.2H_2O$: C, 52.99; H, 5.78; N, 6.87. Found: C, 52.90; H, 5.73; N, 6.85.

EXAMPLE 3

Preparation of (±)-ethyl 4-(aminoiminomethyl)-βS, δR-dihydroxybenzenenonanoate

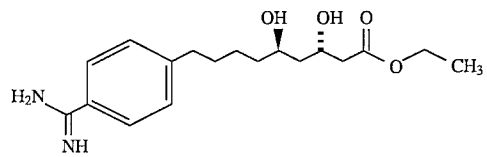

A. Preparation of anti-ethyl 9-(4-cyanophenyl)-3,5-dihydroxynonanoate

The title compound was prepared from the product of example 1, step C (1.87 g, 10 mmol) in a manner similar to example 1, step D substituting ethyl acetoacetate (1.30 g, 10 mmol) in place of methyl acetoacetate. The intermediate hydroxy-keto ester was purified by silica gel chromatography (EtOAc:hexane 1:1) giving 2.54 g of partionally purified product. The carbonyl was stereoselectively reduced using tetramethylammonium triacetoxyborohydride (D. A. Evans, 1988). Thus, tetramethylammonium triacetoxyborohydride (16.6 g, 63.12 mmol) was dissolved in 1:1 acetonitrile: acetic acid (40 mL) and stirred at room temperature for 30 minutes, then cooled to −40° C. The hydroxy-keto ester (2.5 g, 7.89 mmol) in acetonitrile (10 mL) and the solution stirred at −40° C. for 2 hours then at −10° C. for 3 hours. The reaction was quenched by the addition of sat'd aq. Na/K tartrate (20 mL) then poured into sat'd aq. NaHCO$_3$ (200mL). Solid NaHCO$_3$ was added carefully until gas evolution ceased then extracted (2X) with EtOAc, dried (MgSO$_4$), filtered and evaporated under reduced pressure. Silica gel chromatography (EtOAc:hexane 6:4) afforded 1.53 g (48% overall). An analytical sample was prepared by crystallizing from diisopropyl ether (m.p. 86.5°–87.5° C.). Anal. calc'd. for $C_{18}H_{25}NO_4$: C, 67.69; H, 7.89; N, 4.39. Found: C, 68.14; N, 4.37.

$^1$H-NMR (300 MHz, CDCl$_3$) δ 1.28 (t, J=7Hz, 3HN), 1.30–1.73 (m, 8HN), 2.45 (dd, J=5 Hz, J=13 Hz, 1H), 2.53 (dd, J=7 Hz, J=13 Hz, 1H), 2.68 (t, J=7 Hz, 2H), 3.91 (m, 1H), 4.18 (q, J=7 Hz, 2H), 4.36 (m, 1H), 7.27 (d, J=8 Hz, 2H), 7.57 ( d, J=8 Hz, 2H).

B. Preparation of (±)-ethyl 4-aminoiminomethyl)-βS, δR-dihydroxybenzenenonanoate The title compound was prepared from the product of step A (1.50 g, 4.70 mmol) in a manner similar to example 1, step G affording 830 mg (39%) of product as the TFA salt after reverse phase chromatography and trituration of the product with acetonitrile (m.p. 158°–160° C.).

Anal. calc'd. for $C_{20}H_{29}N_2O_6F_3 0.25H_2O$: C, 52.80; H, 6.54; N, 6.16.
Found: C, 52.70; H, 6.36; N, 6.29.

EXAMPLE 4

Preparation of (±)-cis-6-[4-(4-(Aminoiminomethyl)phenyl)butyl]-4-ethenyl-tetrahydro-2H-pyran-2-one, trifluoroacetate

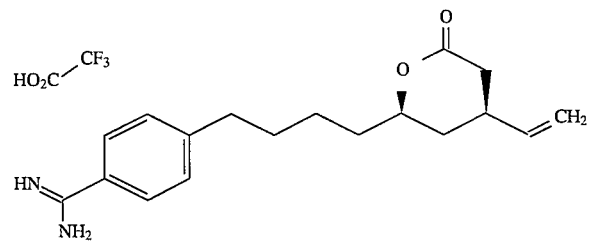

A. Preparation of 6-[4-(4-cyanophenyl)butyl]-5,6-dihydro-2H-pyran-2-one

To a solution of the product of example 1, step F (2.22 g, 8.13 mmol) and triethylamine (2.06 g, 20.40 mmol) in CH$_2$Cl$_2$ (40 mL) at 0° C. was added methanesulfonyl Chloride (930 mg, 8.13 mmol). The reaction was stirred for 10 minutes at 0° C. then at ambient temperature for 2.5 hours. The reaction mixture was concentrated under reduced pressure, partitioned between EtOAc and 1N NaHSO$_4$, then washed successively with 10% K$_2$CO$_3$, brine and dried (MgSO$_4$). Evaporation of the solvent and silica gel chromatography (EtOAc:hexane 1:1) afforded 608 mg (30%) of product (m.p. 66°–69° C.).

Anal. calc'd. for $C_{16}N_{17}NO_2$: C, 75.27; H, 6.71; N, 5.49.
Found: C, 75.00; H, 6.79; N, 5.46.

B. Preparation of trans-6-[4-(4-cyanophenyl)butyl)-4-ethenyl-3,4,5,6-tetrahydro-2H-pyran-2-one To a stirred solution of vinyltributyltin (7.45 g, 23.52 mmol) in dry THF (15 mL) at −78° C. under an atmosphere of nitrogen was added dropwise a 1.6 M solution of nBuLi (14.7 mL, 23.52 mmol) in hexane. After 10 minutes at −78° C., solid CuCN was added all at once under a stream of nitrogen. The mixture was slowly warmed to −30° C. over 45 minutes during which time the CuCN dissolved. The resulting solution was cooled to −60° C. and the product of step A (1.50 g, 5.88 mmol) in THF (10 mL) was added. The solution was warmed to −20° C. over 30 minutes then poured into a rapidly stirred solution of dilute aq. NH$_4$OH/NH$_4$Cl and stirred for 15 minutes. The aqueous phase was extracted with Et$_2$O, dried (MgSO$_4$), filtered and evaporated under reduced pressure. The tetrabutyltin biproduct was simply removed by stirring the residue with hexane and carefully decanting the solvent (repeated 2X), affording 1.52 g (92%) of title product of sufficient purity to be used in the next reaction.

$^1$N-NMR (300 MHz, CDCl$_3$) 81.25–1.85 (m, 8H), 2.47 (dd, J=7 Hz, J=17 Hz, 1H) , 2.60 (dd, J=5 Hz, J=17Hz, 1H) , 2.68 (t, J=7 Hz, 2H), 2.76 (m, 1H), 4.34 (m, 1H), 5.02–5.18 (m, 2H), 5.75–5.89 (m, 1H), 7.27 (d, J=8 Hz, 2H), 7.57 (d, J=8 Hz, 2H).

C. Preparation of cis-6-[4-(4-cyanophenyl)butyl]-4 ethenyl-3,4,5,6-tetrahydro-2H-pyran-2-one To a solution of the product of step B (1.52 g, 5.47 mmol) in 15 mL of MeOH:THF (2:1) was added 1H NaOH (5.9 mL, 5.9 mmol) and the reaction stirred at room temperature for 1.5 hours. The reaction was diluted with water and washed with Et$_2$O. The aqueous phase was acidified with 1H NaHSO$_4$, extracted with EtOAc, dried (MgSO$_4$), filtered and evaporated under reduced pressure. The residue and Ph$_3$P (1.86 g, 7.11 mmol) was immediately dissolved in dry THF (20 mL) and cooled to −40° C. Neat diethyl azodicarboxylate (1.27 g, 7.42 mmol) was added dropwise via syringe and the solution stirred at −40° C. for 3 hours. Concentration of the solvent under reduced pressure and silica gel chromatography (EtOAc:hexane 4:6) of the residue afforded 1.05 g (69%) of the title product as a colorless oil. NMR spectrum analysis indicated the product was contaminated with ~10% of the trans isomer. $^1$H-NMR (300 MHz, CDCl$_3$) δ 1.25–1.80 (m, 7H), 1.90–2.00 (m, 1H), 2.24 (dd, J=11Hz, J=17 Hz, 1H), 2.55–2.79 (m, 4H), 4.30 (m, 1H) 5.02–5.14 (m, 2H), 5.66–5.80 (m, 1H), 7.27 (d, J=8 Hz, 2H), 7.57 ( d, J=8 Hz, 2H).

D. Preparation of (±)-cis-6-[4-(4-(aminoiminomethyl)phenyl)butyl]-4-ethenyl-tetrahydro-2H-pyran-2-one The title compound was prepared from the product of step C (1.00g, 3.53 mmol) in a manner similar to example 1 step G with a modification in the purification. The residue was dissolved in acetonitrile and TFA (402 mg, 3.53 mmol) was added. The solvent was evaporated under reduced pressure and the residue redissolved in a minimal amount of acetonitrile. Addition of Et$_2$O caused the precipitation of the crude product which was filtered and washed with Et$_2$O. The material was briefly suspended in ice water, filtered, washed with ice water and dried. Recrystallization from acetonitrile afforded 720 mg (50%) of product as the TFA salt (m.p. 186°–187° C. dec.). Anal. calc'd. for $C_{20}N_{25}O_4F_3 0.3H_2O$: C, 57.14; H, 6.15; N, 6.66.
Found: C, 57.17; H, 6.30; N, 6.59.

EXAMPLE 5

Preparation of (±)-cis-methyl 2-[4-[4-(aminoiminomethyl)phenyl]butyl]tetrahydro-6-oxo-2H-pyran-4-acetate

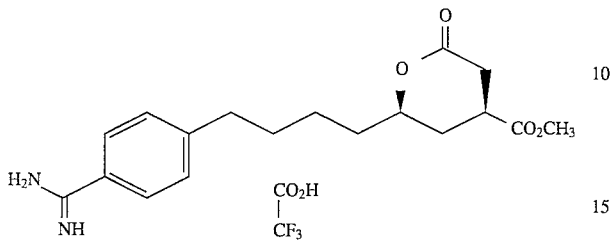

A. Preparation of trans-6-[4-(4-cyanophenyl)butyl]-4-[2-methoxy-2-oxo-1-(phenylsulphonyl)ethyl]3,4,5,6-tetrahydro-2H-pyran-2-one To a solution of the product of example 4, step A (2.00 g, 7.83 mmol) and methyl phenylsulphonylacetate (2.01 g, 9.41 mmol) in 15 mL of tBuOH:DMSO (3:8) stirred at room temperature under an atmosphere of nitrogen was added solid KOtBu (180 mg, 1.61 mmol). The resulting solution was stirred at room temperature for 18 hours, poured into EtOAc, washed successively with 1N NaHSO$_4$, water, brine and dried (MgSO$_4$). The solvent was removed under reduced pressure and silica gel chromatography (EtOAc:hexane 1:1) of the residue afforded 3.01 g (82%) of the title product as oil. NMR spectrum analysis indicated a 1:1 mixture of phenylsulphone diastereomers.

$^1$N-NMR (300 MHz, CDCl$_3$) δ 3.00 (m, 1H), 3.50, 3.59(2 s, OMe), 3.97, 4.00(2 d, J=7 Hz, J=9 Hz, 1H, PhSO$_2$CHRCO$_2$R), 4.36, 4.47 (2 m, 1H, H$_6$), 7.27 (m, 2H), 7.53–7.67 (m, 4H), 7.73 (t, J=8 Hz, 1H), 7.89 (m, 2H).

B. Preparation of cis-6-[4-(4-cyanophenyl)butyl]-4-[(2-methoxy-2-oxo)ethyl]-3,4,5,6-tetrahydro-2H-pyran-2-one To a solution of the product of step A (2.76 g, 5.88 mmol) in 60 mL of MeOH:THF (1:1) at room temperature under an atmosphere of nitrogen was added solid Na$_2$HPO$_4$ (10.02 g, 70.60 mmol). To this mechanically stirred mixture was added powdered 6% Na(Hg) (25.5 g, 66 mmol) in 3 portions over 3 hours. The mixture was stirred at room temperature for an additional 2 hours then quenched with aq. 0.4N tartaric acid (200 mL). The mixture was diluted with water and extracted with EtOAc (2X), dried (MgSO$_4$), filtered and evaporated under reduced pressure. Silica gel chromatography of the residue (EtOAc:CH$_2$Cl$_2$ 1:4) afforded 1.40 g (72%) of product as an oil. NMR spectrum analysis indicates a 4:1 mixture of cis/trans isomers.

$^1$N-NMR (300 MHz, CDCl$_3$) δ 1.15 (m, 1H), 1.35–1.75 (m, 6H), 2.00 (m, 1H), 2.13 (dd, J=10 Hz, J=17 Hz, 1H), 2.35 (d, J=7 Hz, 2H), 2.38–2.52 (m, 1H), 2.68 (t, J=7 Hz, 2H), 2.77 (dd, J=5 Hz, J=17 Hz, 1H), 3.70 (s,3H), 4.30 (m, 1H), 7.28 (d, J=8 Hz, 2H), 7.57 (d, J=8 Hz, 2H).

C. Preparation of (±)-cis-methyl 2-[4-[4-(aminoiminomethyl)phenyl]butyl]tetrahydro-6-oxo-2H-pyran-4-acetate The title compound was prepared from the product of step B (1.40 g, 4.25 mmol) in a manner similar to example 1, step G with a modification in the purification. The residue was dissolved in acetonitrile and TFA (910 mg) was added. The solvent was concentrated under reduced pressure and the residue redissolved in a minimal amount of acetonitrile. The crude product was precipitated by the addition of Et$_2$O, filtered and washed with Et$_2$O. The dry filtercake was washed with ice water and dried. Reprecipitation from CH$_3$CN/Et$_2$O gave 1.25 g (64%) of title product as a 4:1 mixture of cis/trans isomers (m.p. 161°–165° C.).

Anal. calc'd. for C$_{21}$N$_{27}$N$_2$O$_6$F$_3$0.3H$_2$O: C, 54.08; H, 5.98; N, 6.01.
Found: C, 53.95; H, 5.87; N, 6.01

EXAMPLE 6

Preparation of (±)-cis-6-[4-[4-(aminoiminomethyl)phenyl]butyl]tetrahydro-4-[(phenylsulfonyl)methyl]-2H-pyran-2-one, trifluoroacetate

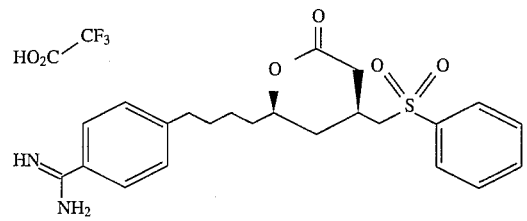

A. Preparation of trans-6-[4-(4-cyanophenyl)butyl]-4-phenylsulfonylmethyl-3,4,5,6-tetrahydro-2H-pyran-2-one A solution of the product of example 5, step A (2.74 g, 5.84 mmol) and sodium chloride (370 mg, 63 mmol) in 4.5 mL of DMSO (containing 1.6% water) was stirred in a 165° C. oil bath for 1.5 hours then at 180° C. for 30 minutes. The reaction mixture was cooled, diluted with EtOAc and washed successively with 1N HCl, water, brine and dried (Na$_2$SO$_4$). Evaporation of the solvent under reduced pressure and silica gel chromatography (EtOAc:hexane 1:1) of the residue afforded 1.12 g (47%) of gummy product.

$^1$N-NMR (300 MHz, CDCl$_3$) δ 1.35–1.83 (m, 6H), 1.90–2.10 (m, 2H), 2.38 (m, 1H), 2.60–2.80 (m, 4H), 3.02–3.20 (m, 2H), 4.40 (m, 1H), 7.27 (d, J=8 Hz, 2H), 7.55–7.67 (m, 4H), 7.72 (t, J=8 Hz, 1H), 7.92 (d, J=7 Hz, 2H).

B. Preparation of cis-6-[4-(4-cyanophenyl)]butyl]-4-phenylsulfonylmethyl-3,4,5,6-tetrahydro-2H-pyran-2-one The title compound was prepared from the product of step A (1.18 g, 2.87 mmol) in a manner similar to example 4, step C affording 1.00 g (85%) of product after silica gel chromatography (EtOAc:hexane 1:1).

$^1$H-NMR (300 MHz, CDCl$_3$) δ 1.35–1.75 (m, 7H), 2.20–2.34 (m, 2H), 2.60–2.75 (m, 3H), 2.85 (ddd, J=2 Hz, J=6 Hz, J=17 Hz, 1H), 4.29 (m, 1H), 7.27 (d, J=8 Hz, 2H), 7.53–7.65 (m, 4H), 7.90 (t, J=Hz, 1H), 7.91 (d, J=7 Hz, 2H).

C. Preparation of (±)-cis-6-[4-[4-(aminoiminomethyl)phenyl]butyl]tetrahydro-4-[(phenylsulfonyl)methyl]-2H-pyran-2-one, trifluoroacetate The title compound was prepared from the product of step B (1.00 g, 2.43 mmol) in a manner similar to example 1, step G affording 910 mg (69%) of product after reverse phase chromatography and trituration with acetonitrile (m.p. 233.5°–234.5° C.).

Anal. calc'd. for C$_{25}$N$_{29}$N$_2$O$_6$F$_3$S: C, 55.34; H, 5.39; N, 5.16; S, 5.91.
Found: C, 55.23; H, 5.36; N, 5.17; S, 6.09.

EXAMPLE 7

Preparation of (±)-trans-6-[4- [4-(Aminoimino)phenyl)butyl]tetrahydro-4-phenyl-2H-pyran-2-one, trifluoroacetate

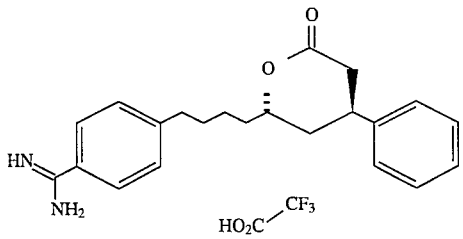

A. Preparation of trans-6-[4-(4-cyanophenyl)butyl]-4-phenyl-3,4,5,6-tetrahydro-2 H-pyran-2 -one The title compound was prepared from the product of example 4, step A (384 mg, 1.50 mmol) in a manner similar to example 4, step B substituting phenyllithium for the n-BuLi/vinyltributyltin combination to give 196 mg (39%) of product after silica gel chromatography (35% EtOAc in hexane).

$^1$N-NMR (300 MHz, CDCl$_3$) δ 1.3–1.85 (m, 6H), 2.04 (m, 2H), 2.67 (t, J=7 Hz, 2H), 2.70–2.85 (m, 2H), 3.34 (pent., J=7 Hz, 1H), 4.37 (m, 1H), 7.15–7.40 (m, 7H), 7.57 (d, J=8 Hz, 2H).

B. Preparation of (±)-trans-6-[4-(Aminoimino)phenyl]butyl] tetrahydro-4-phenyl-2H-pyran-2-one, trifluoroacetate The title compound was prepared from the product of step A (264 mg, 792 mmol) in a manner similar to example 1 step G affording 165 mg (45%) of product as the TFA salt following reverse phase chromatography (m.p. 208°–210° C.).

Anal. calc'd. for $C_{24}N_{27}N_2O_4F_3$: C, 62.06; H, 5.86; N, 6.03. Found: C, 62.08; H, 5.93; N, 6.03.

EXAMPLE 8

Preparation of (±)-cis-6-[4-[4-Aminoiminomethyl)phenyl)butyl]tetrahydro-4-phenyl-2H-pyran-2-one, trifluoroacetate

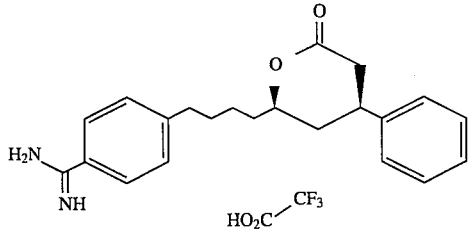

A. Preparation of 7-(4-cyanophenyl)-3-hydroxy-1-phenyl-heptan-1 one

To a solution of diisopropylamine (1.01 g, 10 mmol) in dry THF (20 mL) at 0° C. under an atmosphere of nitrogen was added a 1.6M solution of n-BuLi (6.25 mL, mmol) in hexane. After 15 minutes at 0° C. the solution was cooled to –78° C. and acetophenone (1.2 g, mmol) was added dropwise via syringe. After 10 minutes a solution of the product of example 1 step C (1.87 g, 10 mmol) in 10 mL of THF was added via cannula. The solution was stirred at –78° C. for 30 minutes then poured into 1N NaHSO$_4$, extracted with EtOAc, dried (MgSO$_4$), filtered and evaporated under reduced pressure. Trituration of the residue with hexane afforded 2.54 g (83%) of title product.

$^1$HN-NMR (300 MHz, CDCl$_3$) δ 1.40–1.75 (m, 6H), 2.70 (t, J=7 Hz, 2H), 3.03 (dd, J=9 Hz, J=18 Hz, 1H), 3.16 (dd, J=4 Hz, J=18 Hz, 1H), 4.22 (m, 1H), 7.27 (d, J=8 Hz, 2H), 7.40–7.65 (m, 5H), 7.95 (d, J=8 Hz, 2H).

B. Preparation of 3-(2-bromo-1-oxoethoxy)-7-(4-cyanophenyl)-1-phenylheptan-1-one To a solution of the product of step A (2.42 g, 7.88 mmol) and pyridine (7 mL) in Et$_2$O at 0° C. was added bromoacetyl bromide (2.37 g, 11.82 mmol). The mixture was stirred for 1 hour at 0° C. then at room temperature for 30 minutes. The mixture was diluted with Et$_2$O, washed successively with 1N NaHSO$_4$, sat'd NaHCO$_3$ and dried (MgSO$_4$). Evaporation of the solvent under reduced pressure afforded 3.0 g (89%) of title product.

$^1$H-NMR (300 MHz, CDCl$_3$) 61.35–1.80 (m, 6H), 2.68 (t, J=7 Hz, 2H), 3.12 (dd, J=7 Hz, J=18 Hz, 1H), 3.39 (dd, J=7 Hz, J=18 Hz, 1H), 3.76 (s, 2H), 5.49 (pent., J=7 Hz, 1H), 7.26 (d, J=8 Hz, 2H), 7.49 (t, J=8 Hz, 1H), 7.52–7.63 (m, 4H), 7.94 (d, J=8 Hz, 2H).

C. Preparation of rel-(4R, 6R)-6-[4-(4-cyanophenyl)butyl]-4-hydroxy-4-phenyl-3,4,5,6-tetrahydro-2H-pyran-2-one To a solution of the product of step B (2.71 g, 6.35 mmol) in dry THF (50 mL) at –78° C. under an atmosphere of nitrogen was added a 0.1 M solution of SmI$_2$ (135 mL, 13.5 mmol) over 10 minutes. The blue solution was stirred at –78° C. for 1 hour, poured into dilute aq. HCl, extracted with EtOAc, washed with sat'd NaHCO$_3$, dried (MgSO$_4$), filtered, and the solvent evaporated under reduced pressure. Silica gel chromatography (35–50% EtOAc/hexane) afforded 1.90 g (86% ) of title product.

$^1$H-NMR (300 MHz, CDCl$_3$) δ 1.40–1.90 (m, 6H), 1.99 (dd, J=13 Hz, J=15 Hz, 1H), 2.11 (dd, J=2 Hz, J=15Hz, 1H), 2.60 (t, J=7 Hz, 2H), 2.90 (s, 2H), 4.83 (m, 1H), 7.27 (d, J=8 Hz, 2H), 7.30–7.47 (m, 5H), 7.57 (d, J=8 Hz, 2H).

D. Preparation of cis-6-[4-(4-cyanophenyl) butyl]-4-phenyl-3,4,5,6-tetrahydro-2H-pyran-2-one To a solution of the product of step C (1.90 g, 5.46 mmol) and pyridine (948 mg, 12.01 mmol) in CN$_2$Cl$_2$ (30 mL), cooled in an ice bath, was added slowly, dropwise thionyl chloride (715 mg, 6.01 mmol). The ice bath was removed and the solution stirred at room temperature for 30 minutes. Extractive work up and silica gel chromatography (CN$_2$Cl$_2$) afforded 1.35 g (75%) of product as a mixture of olefin isomers. The material was dissolved in EtOAc (20 mL) and 5% Pd on CaCO$_3$ was added. The mixture was stirred under a balloon of hydrogen for 48 hours. The catalyst was removed and the solvent evaporated under reduced pressure. Silica gel chromatography (EtOAc:CN$_2$Cl$_2$:hexane 3:2:5) afforded 1.35 g (99%) of title product.

$^1$N-NMR (300 MHz, CDCl$_3$) δ 1.40–1.85 (m, 7H), 2.12 (m, 1H), 2.54 (dd, J=11 Hz, J=18 Hz, 1H), 2.69 (t, J=7 Hz, 2H), 2.41 (ddd, J=3 Hz, J=7 Hz, J=17 Hz, 1H), 3.17 (m, 1H), 4.40 (m, 1J), 7.29 (d, J=8 Hz, 2H), 7.22–7.40 (m, 5H), 7.57 (d, J=8 Hz, 2H).

E. Preparation of (±)-cis-6-[4-[4-(Aminoimino)phenyl)butyl]-tetrahydro-4-phenyl-2H-pyran-2-one, trifluoroacetate The title compound was prepared from the product of step D (1.34 g, 3.51 mmol) in a manner similar to example 1, step G affording 720 mg (44%) of product as the TFA salt following reverse phase chromatography (m.p.204°–205° C. dec.).

Anal. calc'd. for $C_{24}H_{27}N_2O_4F_3 \cdot 0.25H_2O$: C, 61.46; H, 5.91; N, 5.97.

Found: C, 61.33; H, 5.80; N, 6.02.

EXAMPLE 9

Preparation of rel-(4R, 6R)-6-[4-(4-(Aminoiminomethyl)phenyl)butyl]-4 -hydroxy-4-methyl-3,4,5,6-tetrahydro-2H-pyran-2-one

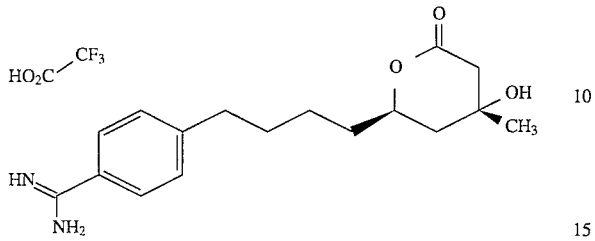

A. Preparation of 8-4-cyanophenyl)-4-hydroxy-2-methyl-1-octene.

To a solution of the product of example 1, step C (2.80 g, 15 mmol), and methallyl chloride (2.72 g, 30 mmol) in DMF (20 mL) was added NaI (4.50 g, 30 mmol) and zinc dust. The mixture was stirred at ambient temperature for 2 hours, diluted with aq. 10% HCl and extracted with EtOAc (2X). The organic layer was washed with brine, dried (MgSO$_4$), filtered and evaporated under reduced pressure. Silica gel chromatography (CH$_2$Cl$_2$) afforded 3.60 g (99%) of title product.

$^1$H-NMR (300 MHz, CDCl$_3$) δ 1.35–1.70 (m, 6H), 1.76 (s, 3H), 2.08 (dd, J=9 Hz, J=14 Hz, 1H), 2.19 (dd, J=4 Hz, J=14 Hz, 1H), 2.69 (t, J=7 Hz, 2H), 3.71 (m, 1H), 4.80 (s, 1H), 4.89 (s, 1H), 7.27 (d, J=8 Hz, 2H), 7.57 (d, J=8 Hz, 2H).

B. Preparation of 8-(4-cyanophenyl)-4-(2-bromo-1-oxoethoxy)-octane-2-one

Ozone was passed through a solution of the product of step A (1.14 g, 4.69 mmol) in MeOH (20 mL) at −78° C. until a blue color persisted. After 10 minutes, oxygen was bubbled through the solution until the blue color dissipated then dimethylsulfide (1.0 mL) was added and the reaction mixture allowed to warm to room temperature while stirring overnight. The solvent was removed under reduced pressure. To a solution of the crude residue and pyridine (741 mg, 9.38 mmol) in Et$_2$O at 0° C. was added dropwise bromoacetyl bromide (1.04 g, 5.16 mmol). The reaction was allowed to warm to 15° C. over 1.5 hours then diluted with EtOAc and washed successively with 1N NaSO$_4$ and sat'd NaHco$_3$, dried (MgSO$_4$), filtered and evaporated under reduced pressure to give 1.00 g of crude product used directly in the next reaction.

$^1$H-NMR (300 MHz, CDCl$_3$) δ 1.30–1.75 (m, 6H), 2.17 (s, 3H), 2.55–2.72 (m, 3H), 2.79 (dd, J=8 Hz, J=17 Hz, 1H), 3.77 (s, 2H), 5.29 (m, 1H), 7.26 (d, J=8 Hz, 2H, 7.57 ( d, J=8 Hz, 2H).

C. Preparation of rel-(4R, 6R) -6-[4-(4-cyanophenyl)butyl]-4-hydroxy-4-methyl-3,4,5,6-tetrahydro-2H-pyran-2-one The title compound was prepared from the product of step B (2.66 g, 7.33 mmol) in a manner similar to example 8, step C to give 1.88 g (90%) of product after silica gel chromatography (EtOAc:CN$_2$Cl$_2$1:4).

$^1$H-NMR (300 MHz, CDCl$_3$) δ 1.33 (s, 3H), 1.40–1.75 (m, 7H), 1.86 (m, 1H), 2.42 (d, J=18 Hz, 1H), 2.60–2.72 (m, 3H), 4.65 (m, 1H), 7.27 (d, J=8 Hz, 2H), 7.57 (d, J=8 Hz, 2H).

D. Preparation of rel-(4R, 6R)-6-[4-(4-(aminoiminomethylphenyl]butyl]-4-hydroxy-4-methyl-3,4,5,6-tetrahydro-2H-pyran-2-one The title compound was prepared from the product of step C (1.83 g, 6.44 mmol) in a manner similar to example 1, step G to give 1.71 g (63%) of the title product as the TFA salt following reverse phase chromatography (m.p. 195°–196° C.).

Anal. calc'd. for C$_{19}$H$_{25}$N$_2$O$_5$F$_3$: C, 54.54; H, 6.02; N, 6.70. Found: C, 54.57; H, 5.99; N, 6.69.

EXAMPLE 10

Preparation of (±)-cis-6-[4-[4-(Aminoiminomethyl)phenyl)butyl]tetrahydro-4-methyl-2H-pyran-2-one, trifluoroacetate

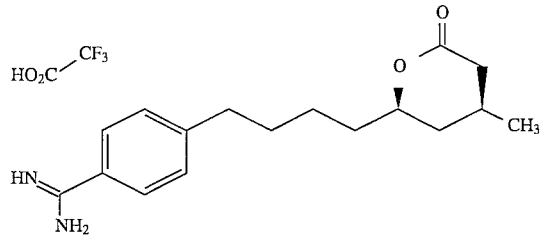

A. Preparation of 6-[4-(4-(aminoiminomethyl)phenyl)butyl]-4-methyl-tetrahydro-2H-pyran-2-one To a solution of the product of example 9, step D (500 mg, 1.20 mmol) in 10 mL of TFA:1,2-dichloroethane (6:4) was added trifluoroacetic anhydride (1.00 g, 4.78 mmol). The solution was stirred at 60° C. for 30 minutes, concentrated under reduced pressure. The residue was purified by reverse phase chromatography on a Waters® OR C-18 Delta Pak column using a 0.05% TFA/water:acetonitrile gradient affording 360 mg (75%) of product (m.p. 188°–191° C. dec.).

Anal. calc'd. for C$_{19}$H$_{23}$N$_2$O$_4$F$_3$: C, 56.99; H, 5.79; N, 7.00. Found: C, 56.61; H, 5.72; N, 6.95.

B. Preparation of (±)-cis-6-[4-[4-(Aminoiminomethyl)phenyl]butyl]tetrahydro-4-methyl-2H-pyran-2-one, trifluoroacetate A solution of the product of step A (1.00 g, 2.5 mmol) and 10% Pd/C (50 mg) in MeOH (10 mL) was stirred under a balloon of hydrogen for 3 hours. The catalyst was removed and the solvent evaporated under reduced pressure. Recrystallization of the product from acetonitrile afforded 560 mg (56%) of product (m.p. 206°–207.5° C. dec.).

Anal. calc'd. for C$_{19}$H$_{25}$N$_2$O$_4$F$_3$: C, 56.71; H, 6.26; N, 6.96. Found: C, 56.28; H, 6.25; N, 6.95.

EXAMPLE 11

Preparation of (±)-cis-6-[4-[4-(Aminoiminomethyl)phenyl)butyl]tetrahydro-4-(3-pyridinyl-2H-pyran-2-one, ditrifluoroacetate

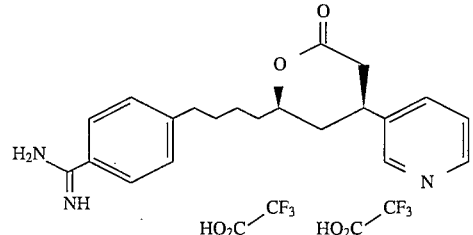

A. Preparation of 7-(4-cyanophenyl)-3-hydroxy-1-(3-pyridyl)heptan-1-one

To a solution of diisopropylamine (1.01 g, mmol) in dry THF (20 mL) at 0° C. under an atmosphere of nitrogen was added a 1.6M solution of nBuLi (6.25 mL, 10 mmol) in hexane. After 15 minutes at 0° C. the solution was cooled to −78° C. and 3-acetylpyridine (1.21 g, 10 mmol) was added dropwise via syringe. After 10 minutes a solution of the product of example 1 step C (1.87 g, 10 mmol) in 10 mL of THF was added via canula. The solution was stirred at −78° C. for 30 minutes then poured into water (50 mL) and 1N NaHSO$_4$ (20 mL), extracted with EtOAc, dried (MgSO$_4$), filtered and evaporated under reduced pressure leaving an oily residue which solidified on standing. Trituration of the residue with diisopropyl ether gave 1.62 g (53%) of the title product (m.p. 93°–97° C.).
Anal. calc'd. for $C_{19}N_{20}N_2O_2$: C, 74.00; H, 6.54; N, 9.08. Found: C, 73.90; H, 6.80; N, 9.06.

B. Preparation of 6-4-(4-cyanophenyl]butyl-4-(3-pyridyl)-5,6-dihydro-2H-pyran-2-one To a solution trimethylsilyl P,P-dimethylphosphonoacetate (2.03 g, 8.44 mmol) and DMF (5 uL) in CH$_2$Cl$_2$ (10 mL) was added oxalyl chloride (2.45 g, 19.47 mmol). The solution was stirred at room temperature until gas evolution ceased (ca. 1 hour). The solvent was removed under reduced pressure and the residue reconstituted with 1,2-dichloroethane and concentrated again under reduced pressure. This residue of the crude P,P-dimethyl phosphonoacetyl chloride in THF (10 mL) was added to a stirred solution of the product of step A (2.00 g, 6.49 mmol) and pyridine (1.03 g, 13.00 mmol) in THF (60 mL) at 0° C. After 10 minutes, the reaction was removed from the ice bath and stirred at room temperature for 1 hour. The reaction mixture was diluted with EtOAc, washed with water, dried (MgSO$_4$), filtered and concentrated under reduced pressure. The unstable phosphonoacetate ester was dissolved in dry THF (50 mL) and cooled to 0° C. under an atmosphere of nitrogen. Solid NaH (60% dispersion in mineral oil) (285 mg, 7.14 mmol) was added all at once under a stream of nitrogen. The reaction was allowed to warm to room temperature over 1 hour then stirred for an additional 1 hour. The mixture was diluted with EtOAc, washed with ½ sat'd NaCl, dried (MgSO$_4$), filtered and evaporated under reduced pressure. Silica gel chromatography (EtOAc) afforded 1.24 g (58%) of product (m.p. 110°–112° C.). Anal. calc'd. for $C_{21}H_{20}N_2O_2$: C, 75.88; H, 6.07; N, 8.43.
Found: C, 75.78; H, 6.04; N, 8.31.

C. Preparation of cis-6-(4-(4-cyanophenyl]butyl-4-(3-pyridyl)-3,4,5,6-tetrahydro-2H-pyran-2-one To a stirred solution of the product of step B (1.50.g, 4.52 mmol) in EtOAc (30 mL) was added 5% Pd/C (1.50 g) and the mixture stirred under a balloon of hydrogen at room temperature for 20 hours. The reaction was incomplete as determined by thin layer chromatography, thus an additional 500 mg of catalyst was added and the reaction stirred for an additional 20 hours. The catalyst was removed and the solvent evaporated under reduced pressure. Silica gel chromatography (EtOAc) afforded 870 mg (58%) of the title product.
$^1$H-NMR (300 MHz, CDCl$_3$) 61.30–1.85 (m, 7H), 2.15 (m, 1H), 2.53 (dd, J=12 Hz, J=18 Hz, 1H), 2.70 (t, J=7 Hz, 2H), 2.94 (ddd, J=2 Hz, J=6 Hz, J=18 Hz, 1H), 3.24 (m, 1H), 4.43 (m, 1H), 7.25–7.35 (m, 3H), 7.53 (dt, J=2 Hz, J=8 Hz, 1H), 7.58 (d, J=8 Hz, 2H), 8.50 (d, J=2 Hz, 1H), 8.55 ( dd, J=2 Hz, J=5 Hz, 1H).

D. Preparation of (±)-cis-6-[4-[4-(Aminoiminomethyl)phenyl)butyl]tetrahydro-4-(3-pyridinyl)-2H-pyran-2-one, ditrifluoroacetate A solution of the product of step C (100 mg, 0.30 mmol) in dry THF (1 mL) was added to a stirred solution of 1.0M lithium bis(trimethylsilyl)amide (1.2 mL, 1.2 mmol) in dry THF (2 mL) at −78° C. under an atmosphere of nitrogen. The cooling bath was removed and the solution stirred at ambient temperature for 17 hours. The reaction was cooled in an ice bath and a solution of aq. 6N HCl (0.40 mL, 2.4 mmol) was added. The ice bath was removed and the mixture was stirred at ambient temperature for 10 minutes. Evaporation of the solvent under reduced pressure and reverse phase chromatography on a Waters® Delta Pak C-18 column using a 0.05% aq. TFA/acetonitrile gradient afforded 60 mg (35%) of product as the bis(TFA) salt [m.p. 106° C. (phase change), 135°–138° C.].
Anal. calc'd. for $C_{25}H_{27}N_3O_6F_6$: C, 51.81; H, 4.70; N, 7.25. Found: C, 51.54; H, 4.77; N, 7.26.

EXAMPLE 12

Preparation of N-[4-(aminoiminomethyl)phenyl] tetrahydro-6-oxo-2H-pyran-2-propanamide, trifluoroacetate

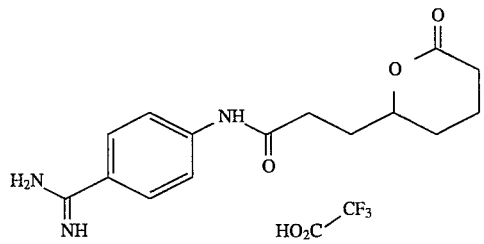

A. Preparation of 6-(3-hydroxy-3-oxopropyl)-3,4,5,6-tetrahydro-2H-pyran-2-one

To a mixture of known (cf. A. Ijima et al., 1971) 6-(3-butenyl)-3,4,5,6-tetrahydro-2H-pyran-2-one (1.20 0g, 11.9 mmol) and NaIO$_4$ (11.50 g, 53.5 mmol) in 88 mL of H$_2$O:CCl$_4$:CH$_3$CN (3:2:2) cooled to −20° C. was added RuCl$_3$H$_2$O (50 mg, 0.24 mmol). The mixture was stirred at −20° C. for 2 hours, diluted with water and extracted with CH$_2$Cl$_2$. The aqueous layer was saturated with NaCl and extracted with EtOAc (4X). The organic layers were combined, dried (MgSO$_4$) and the solvent evaporated under reduced pressure. The residue was filtered through a bed of silica gel (EtOAc:Et$_2$O, 1:1) to afford 1.20 g (84%) of the title product.
$^1$H-NMR (300 MHz, CDCl$_3$) δ 1.50–2.02 (m, 6H), 2.35–2.54 (m, 2H), 2.54–2.65 (m, 2H), 4.37 (m, 1H).

B. Preparation of 6-[3-(4-cyanophenylamino)-3-oxopropyl] -3,4,5,6-tetrahydro-2H-pyran-2-one To a solution of the product of step A (900 mg, 7.50 mmol) in CH$_2$Cl$_2$ (20 mL) was added oxalyl chloride (4.76 g, 37.5 mmol) and the reaction stirred at room temperature until gas evolution ceased (ca. 1.5 hours). The solvent was removed under reduced pressure and the residue evaporated 2 more times for CH$_2$Cl$_2$. A solution of the resulting acid chloride in CH$_2$Cl$_2$ (10 mL) was added to a stirred solution of 4-aminobenzonitrile (885 mg, 7.50 mmol), dimethylaminopyridine (915 mg, 7.50 mmol) and triethylamine (757 mg, 7.50 mmol) in CH$_2$Cl$_2$ (15 mL). The mixture was stirred at room temperature for 18 hours, concentrated under reduced pressure and partitioned between EtOAc and sat'd NaHCO$_3$. The organic layer was washed with 1N NaHSO$_4$, dried (MgSO₄), filtered and evaporated under reduced pressure. Silica gel chromatography (EtOAc:CH₂Cl₂, 1:1) afforded 780 mg (47%) of product (m.p. 145°–148° C.).
Anal. calc'd. for C₁₅H₁₆N₂O₃: C, 66.16; H, 5.92; N, 10.29.
Found: C, 65.92; H, 6.02; N, 10.05.

C. Preparation of 6-[3-(4-(aminoiminomethyl)phenylamino)-3-oxopropyl]-3,4,5,6-tetrahydro-2H-pyran-2-one The title compound was prepared from the product of step B (770 mg, 2.83 mmol) in a manner similar to example 1, step G to give 430 mg (38%) of product as TFA salt after reverse phase chromatography and trituration with CH₃CN/Et₂O (m.p. 151°–153° C. dec.).
Anal. calc'd. for C₁₇H₂₀N₃O₅F0.25N2O: C, 50.06; H, 5.07; N, 10.30.
Found: C, 50.05; H, 4.83; N, 10.45.

EXAMPLE 13

Preparation of 6-[4-(4-(aminoiminomethyl)phenyl)butyl]-tetrahydro-2H-pyran-2-one.

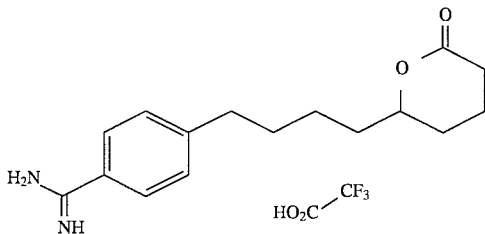

A. Preparation of 6-[4-(4-cyanophenyl)butyl]-3,4,5,6-tetrahydro-2H-pyran-2-one.

A solution of the product of example 4, step A (1.27 g, 0.5 mmol) and 5% Pd on CaCO₃ in EtOAc (50 mL) was stirred under a balloon of hydrogen for 2 days. Evaporation and silica gel chromatography (EtOAc:hexane 1) afforded 850 mg (67%) of product.
¹H-NMR (300 MHz, CDCl₃) δ 1.3–2.0 (m, 10H), 2.44 (m, H), 2.56 (m, 2H), 2.68 (t, J=7 Hz, 2H), 4.26 (m, 1H), 7.27 (d, J=8 Hz, 2H), 7.57 (d, J=8 Hz, 2H).

B. Preparation of 6-[4-(4-(aminoiminomethyl)phenyl)butyl]-3,4,5,6-tetrahydro-2H-pyran-2-one.

The title compound was prepared from the product of step A (850 mg, 3.31 mmol) in a manner similar to example 1, step G, affording 710 mg (55%) of product as the TFA salt after reverse phase chromatography and precipitation from acetonitrile/ether (m.p. 207°–208.5° C.).
Anal. calc'd. for C₁₈H₂₃N₂O₄F₃: C, 55.66; H, 5.97; N, 7.21.
Found: C, 55.31; H, 6.12; N, 7.17.

EXAMPLE 14

Preparation of (±)-trans-6-[4-[4-(aminiminomethyl)phenyl)-3-butynyl)]-4-(4-ethoxyphenyl)-tetrahydro-2H-pyran-2-one.

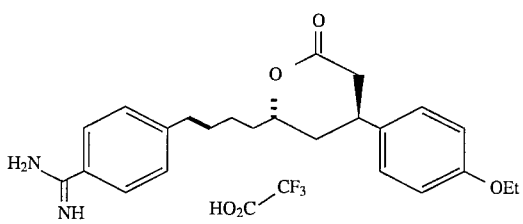

A. Preparation of 5-(4-cyanophenyl)-4-pentynal.

The title compound was prepared from the product of example 1, step A (4.39 g, 23.73 mmol) in a manner similar to example 1, step C, substituting 5-(4-cyanophenyl)-4-pentynol for 5-(cyanophenyl)pentanol. Extractive workup affordeod 4.40 g (100%) of crude product used immediately in the next reaction.
¹H-NMR (300 MHz, CDCl₃) δ 2.70–2.86 (m, 4H), 7.45 (d, J=8 Hz, 2H), 7.57 (d, J=8 Hz, 2H), 9.85 (s, 1H).

B. Preparation of (cis/trans)-9-(4-cyanophenyl)3,5-dihydroxy-8-nonynoic acid.

The title compound was prepared from the product of step A (4.34 g, 23.73 mmol) in a manner similar to example 1, step D. The residue was dissolved 50 mL of THF:MeOH (1:1) and 25 mL of 1N NaOH was added. The reaction mixture was stirred at room temperature for 2 hours, diluted with water and extracted with ether. The aqueous phase was acidified with IN NaHSO₄, extracted with EtOAc, dried (MgSO₄), filtered and evaporated under reduced pressure affording 4.83 g of crude product used directly in the next reaction.
¹H-NMR (300 MHz, CDCl₃) δ 1.60–1.85 (m, 4H), 2.50–2.64 (m, 4H), 4.07–4.15 (m, 1H), 4.30–4.47 (m, 1H), 7.45 (d, J=8 Hz, 2H), 7.57 ( d, J=8 Hz, 2H).

C. Preparation of 6-[4-(4-cyanophenyl)-3-butynyl]5,6-dihydro-2H-pyran-2-one.

To a solution of the product of step B (4.60 g, 16.03 mmol) and triethylamine (9.70 g, 96.16 mmol) in CH₂Cl₂ (50 mL) at 0° C. was added methanesulfonyl chloride (4.57 g, 40.07 mmol). The reaction mixture was warmed to room temperature and stirred for 2 hours, diluted with CH₂Cl₂ and washed with iN NaHSO₄, dried (MgSO₄), filtered and evaporated under reduced pressure. Silica gel chromatography (EtOAc/hexane 1:1) of the residue afforded 850 mg (21%) of product.
¹H-NMR (300 MHz, CDCl₃) δ 1.90–2.02 (m, 1H), 2.04–2.17 (m, 1H), 2.42 (m, 2H), 2.70 (m, 2H), 4.62 (m, 1H), 6.07 (dt, J=10 Hz, J=2 Hz, 1H), 6.92 (dt, J=10 Hz, J=5 Hz, 1H), 7.45 (d, J=8 Hz, 2H), 7.57 (d, J=8 Hz, 2H).

D. Preparation of (±)-trans-6-[4-(4-cyanophenyl)-3-butynyl]-4-(4-ethoxyphenyl)-tetrahydro-2H-pyran-2 -one.

To a stirred solution of 4-bromophenetole (2.24 g, 11.15 mmol) in dry THF (12 mL) at −70° C. under an atmosphere of nitrogen was added dropwise a 1.6 M solution of n-BuLi (6.97 mL, 11.15 mmol) in hexane. After 15 minutes at −70° C., solid CuCN (499 mg, 5.57 mmol) was added all at once under a stream of nitrogen. The reaction was stirred at −60° C. for 30 minutes then cooled to −70° C. To the resulting solution was added the product of step C (700 mg, 2.79 mmol) in THF (5 mL) and stirred at −70° C. for 30 minutes. The reaction mixture was poured into a rapidly stirred solution of aqueous NH₄OH/NH₄Cl, extracted with EtOAc, washed with water, dried (MgSO₄), filtered and evaporated under reduced pressure. Silica gel chromatography ( 35% EtOAc/hexane) afforded 480 mg (46%) of product.
¹H-NMR (300 MHz, CDCl₃) δ 1.42 (t, J=7 Hz, 3H), 1.80–1.91 (m, 1H), 2.00–2.13 (m, 3H), 2.65 (t, J=7 Hz, 2H), 2.70–2.87 (m, 2H), 3.35 (pent, J=7 Hz, 1H), 4.00 (q, J=7 Hz, 2H), 4.56 (m, 1H), 6.86 (d, J=8 Hz, 2H), 7.12 (d, J=8 Hz, 2H), 7.37 (d, J=8 Hz, 2H), 7.57 (d, J=8 Hz, 2H).

E. Preparation of (±)-trans-6-[4-(4-(aminiminomethyl)phenyl)-3-butynyl]-4-(4-ethoxyphenyl)-tetrahydro-2H-pyran-2-one.

The title compound was prepared from the product of step D (480 mg, 1.29 mmol) in a manner similar to example 1, step G affording 283 mg( 43 % ) of product as the TFA salt after reverse phase chromatography and precipitation from CH₂Cl₂/Et₂O.

Anal. calc'd. for $C_{26}H_{27}N_2O_5F_3$: C, 59.97; H, 5.58; N, 5.38. Found: C, 60.33; H, 5.43; N, 5.29.

EXAMPLE 15

Preparation of (±)-cis-6-[4-(4-(aminoiminomethyl)phenyl)butyl]-4-cyclohexyl-3,4,5,6-tetrahydro-2H-pyran-2-one, trifluoroacetate.

A. Preparation of (±)-7-(4-cyanophenyl)-3-hydroxy-1-cyclohexylheptane-1-one.

The title compound is prepared in a manner similar to example 8, step A, substituting cyclohexyl methyl ketone for acetophenone.

B. Preparation of (±)-cis-6-[4-(4-aminoiminomethyl)phenyl)butyl]-4-cyclohexyl-3,4,5,6-tetrahydro-2H-pyran-2-one, trifluoroacetate.

The title compound is prepared from the product of step A by sequentially applying the methods described in the following examples: example 8, steps B and C; example 1, step G; example 10, steps A and B.

EXAMPLE 16

Preparation of (±)-cis-6-[4-(4-aminoiminomethyl)phenyl)butyl]-4-[(methylsulfonyl)methyl] -3,4,5,6-tetrahydro-2H-pyran-2-one, trifluoroacetate.

A. Preparation of (±)-trans-6-[4-(4-cyanophenyl)butyl]-4-[(methylsulfonyl)methyl]-3,4,5,6-tetrahydro-2H-pyran-2-one The title compound is prepared in a manner similar to example 5, step A, substituting methyl methylsulfonylacetate for methyl phenylsulfonylacetate.

B. Preparation of (±)-cis-6-[4-(4-aminoiminomethyl)phenyl)butyl]-4-[(methylsulfonyl)methyl]-3,4,5,6-tetrahydro-2H-pyran-2-one, trifluoroacetate.

The title compound is prepared from the product of step A by sequentially applying the methods described in the following examples: example 6, step A; example 4, step C; example 1, step G.

EXAMPLE 17

Preparation of N-[4-(aminoiminomethyl)phenyl]3,4,5,6-tetrahydro-6-oxo-4S-hydroxy-2H-pyran-2R-propanamide, trifluoroacetate.

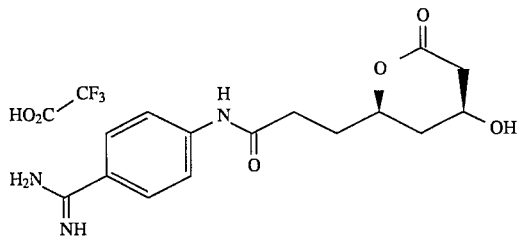

A. Preparation of t-butyl 5R-hydroxy-9-methyl-3-oxo-8-decenoate.

To a 1M solution of lithium bis(trimethylsilyl)amide (25.3 mL, 25.3 mmol) in THF, cooled to −45° C. was added t-butyl acetate (3.4 mL, 25.3 mmol), neat, dropwise via syringe. After 10 minutes, known (c.f. D. F. Taber, L. J. Silverberg, 1991) methyl 3R-hydroxy-7-methyloctanoate (1.47 g, 7.90 mmol) in 5 mL of THF was added and stirred at −45° C. for 1 hour. The reaction was poured into 1N NaHSO$_4$ and extracted (2X) with EtOAc, dried (MgSO$_4$), filtered and evaporated under reduced pressure affording 2.10 g of crude product used directly in the next reaction.

$^1$H-NMR (300 MHz, CDCl$_3$) δ 1.4 ( s, 9H), 1.62 ( s, 3H), 1.69 (s, 3H), 2.10 (q, J=7 Hz, 2H), 2.58–2.77 (m, 2H), 3.39 (2, 2H), 4.07 (m, 1H), 5.11 (t, J=7 Hz, 1H).

B. Preparation of t-butyl 3S,5R-dihydroxy-9-methyl-8-decenoate.

To a solution of tetramethylammonium triacetoxyborohydride (11.83 g, 45 mmol) in 60 mL of HOAc/CH$_3$CN (1:1), cooled to −30° C. was added the product of step A (2.70 g, 10 mmol) in 5 mL CH$_3$CN. The reaction was stirred at −30° C.—20° C. for 2 hours. The reaction was quenced at −30° C. by the addition of 50 mL of ½ saturated aqueous Na/K tartrate. After 15 minutes, the stirred solution was covered with 100 mL of Et$_2$O/hexane (1:1) and NaOH (22 g in 150 mL of H$_2$O) was added slowly. The layers were separated and the aqueous layer was extracted with Et$_2$O/hexane (1:1). The organic layers were combined, washed with saturated NaCl, dried (MgSO$_4$), and evaporated under reduced pressure. Crystalization from cold pet. ether afforded 1.50 g of product as a white solid (m.p. 64.5°–65.5° C.).

Anal. calc'd. for $C_{15}H_{28}O_4$: C, 66.14; H, 10.36. Found: C, 66.49; H, 10.76.

C. Preparation of 3S-hydroxy-6R-(4-methylpent-3-enyl)-3,4,5,6-tetrahydro-2H-pyran-2-one.

To a solution of the product of step B (12.55 g, 46.1 mmol) in 20 mL of MeOH was added NaOH (3.70 g, 92.5 mmol) in 10 mL of water. After stirring at ambient temperature for 2 hours, the reaction was poured into 100 mL of 1N NaHSO$_4$. The aqueous phase was saturated with NaCl and extracted (3X) with EtOAc, dried (MgSO$_4$), and evaporated under reduced pressure. The resulting crude acid was dissolved in benzene and refluxed with azeotropic removal of water for 4 hours. The solvent was removed under reduced pressure and the residue chromatographed on silica gel (50%–70% EtOAC/hexane) to give 9.10 g (99%) of product. $^1$H-NMR (300 MHz, CDCl$_3$) δ 1.61 (s, 3H), 1.69 (s, 3H), 1.72–1.87 (m, 1H), 2.15 (m, 2H), 2.26 (m, 1H), 2.47 (dd, J=16 Hz, J=8 Hz, 1H), 2.90 (dd, J=16 Hz, J=6 Hz, 1H), 4.10–4.31 (m, 2H), 5.08 (t, J=7 Hz, 1H).

D. Preparation of 3S-(t-butyldimethylsiloxy)-6R-(4-methylpent-3-enyl)-3,4,5,6-tetrahydro-2H-pyran-2-one.

To a solution of the product of step C (9.20 g, 46.5 mmol) in 8 mL of DMF was added t-butyldimethylsilyl chloride (7.34 g, 48.8 mmol) and imidazole (6.64 g, 97.6 mmol). The reaction was stirred at ambient temperature for 5 hours, diluted with water and extracted (2X) with hexane. The organic phase was washed with saturated NaCl, dried (MgSO$_4$), filtered, and evaporated under reduced pressure affording 14.54 g (100%) of crude product used directly in the next reaction.

$^1$H-NMR (300 MHz, CDCl$_3$) δ 0.07 (s, 6H), 0.88 (s, 9H), 1.61 (s, 3H), 1.69 (s, 3H), 1.72–1.87 (m, 1H), 2.05–2.20 (m, 3H), 2.42 (dd, J=16 Hz, J=8 Hz, 1H), 2.81 (dd, J=16 Hz, J=6 Hz, 1H), 4.08–4.22 (m, 2H), 5.08 (t, J=7 Hz, 1H).

E. Preparation of 3S-(t-butyldimethylsiloxy)-6R-(2-carboxyethyl)-3,4,5,6-tetrahydro-2H-pyran-2-one.

To a stirred mixture of the product of step D (1.00 g, 3.20 mmol) and sodium metaperiodate (3.08 g, 14.40 mmol) in 28 mL of CCl$_4$/CH$_3$CN/H$_2$O (2:2:3) was added 15 mg of RuCl$_3$·H$_2$O. The reaction mixture was stirred vigorously at ambient temperature for 5 hours, diluted with 50 mL of water and extracted (2X) with Et$_2$O/EtOAc (1:1). The organic phase was washed with saturated NaCl, dried (MgSO$_4$), and filtered through a bed of silica gel using Et$_2$O/EtOAc (1:1) as eluent. Evaporation of the solvent under reduced pressure afforded 940 mg (97%) of crude product as a dark oil used directly in the next reaction.

$^1$H-NMR (300 MHz, CDCl$_3$) δ 0.07 (s, 6H), 0.88 (s, 9H), 1.56–1.67 (m, 1H), 1.88–2.06 (m, 2H), 2.44 (dd, J=16 Hz, J=8 Hz, 1H), 2.61 (t, J=7 Hz, 2H), 2.81 (dd, J=16 Hz, J=6 Hz, 1H), 4.10–4.34 (m, 2H).

F. Preparation of N-(4-(aminiminomethyl)phenyl]3,4,5,6-tetrahydro-6-oxo-4S-hydroxy-2H-pyran-2R-propanamide trifluoroacetate.

To a solution of the product of step E (0.50 g, 1.65 mmol), pyridine (140 mg, 1.75 mmol) and 20 mg of 4-dimethylaminopyridine in 3 mL of CH$_2$Cl$_2$ was added trimethylsilyl chloride (190 mg, 1.75 mmol). After stirring for 15 minutes at ambient temperature, 5 μL of DMF and oxalyl chloride (216 mg, 1.70 mmol) were sequentially added. After stirring for an additional 30 minutes at ambient temperature, the reaction mixture was pipeted into a solution of aminobenzamidine dihydrochloride (343 mg, 1.65 mmol) in 3 mL DMF/pyridine (1:1). The reaction mixture was stirred at ambient temperature for 30 minutes, concentrated under reduced pressure and triturated with Et$_2$O. After decantation of the Et$_2$O from the oily residue, the crude material was dissolved in 10 mL of 48% aq. HF/CH$_3$CN (1:9) and stirred at ambient temperature for 1 hour. The solvent was partially removed under reduced pressure and then triturated with Et$_2$O. Decantation of the Et$_2$O and purification of the residue using reverse phase chromatography on a Waters® C-18 Delta Pak column using a 0.05% TFA/water:acetonitrile gradient afforded 230 mg (33%) of the title compound as the TFA salt after trituration with CH$_3$CN/Et$_2$O [m.p. 222.5°–223.5° C. (dec.)].

Anal. calc'd. for C$_{17}$H$_{20}$N$_3$O$_6$F$_3$·⅓H$_2$O: C, 48.01; H, 4.90; N, 9.88.
Found: C, 47.82; H, 4.70; N, 9.88.

$^1$H-NMR (300 MHz, d$_6$-DMSO) δ 1.35–1.47 (m, 1H), 1.80–2.02 (m, 2H), 2.13–2.31 (m, 2H), 2.40–2.64 (m, 2H), 2.77 (dd, J=16 Hz, J=6 Hz, 1H), 4.10 (m, 1H), 4.29 (m, 1H), 7.80 ( s, 4H).

EXAMPLE 18

The platelet receptor binding affinity and aggregation inhibitory potency of representative compounds of the present invention can be demonstrated by the assays presented below.

In-Vitro Platelet Aggregation in PRP

Healthy male or female dogs were fasted for 8 hours prior to drawing blood; then 30 ml whole blood was collected using a butterfly needle and 30 cc plastic syringe with 3 ml of 0.129M buffered sodium citrate (3.8%). The syringe was rotated carefully as blood was drawn to mix the citrate. Platelet-rich plasma (PRP) was prepared by centrifugation at 975×g for 3.17 minutes at room temperature, allowing the centrifuge to coast to a stop without braking. The PRP was removed from the blood with a plastic pipette and placed in a plastic capped, 50 ml Corning conical sterile centrifuge tube which was held at room temperature. Platelet poor plasma (PPP) was prepared by centrifuging the remaining blood at 2000×g for 15 minutes at room temperature allowing the centrifuge to coast to a stop without braking. The PRP was adjusted with PPP to a count of 2–3×10$^8$ platelets per ml. 400 μl of the PRP preparation and 50 μl of the compound to be tested as prepared below or saline were preincubated for 1 minute at 37° C. in a BioData aggregometer (BioData, Horsham, Pa.). 50 μl of adenosine 5'diphosphate (ADP) (50 μm final concentration) was added to the cuvettes and the aggregation was monitored for 1 minute. The test compounds were prepared by the following procedure. The compound was dissolved in 100% ethanol at a concentration of 10$^{-2}$M. It was vortexed for 30 seconds followed by the addition of 1.1 equivalents of 1N NaOH. This solution was mixed for 30 minutes at room temperature. After the 30 minutes of mixing, the compound solution was brought to a working concentration of 10$^{-3}$M with double distilled water. All compounds are tested in duplicate. Results are calculated as follows:

Percent of control=[(maximal OD minus initial OD of compound) divided by (maximal OD minus initial OD of control saline)]×100. The % inhibition=100 (percent of control).

The compounds tested and their median inhibitory concentrations (ICs$_{50}$) are recorded in Table A. IC$_{50}$'s (if a compound showed 50% inhibition) were calculated by linear regression of the dose response curve. The assay results for the representative compounds of the present invention are set forth in Table A. Also in Table A, two readings given in a single box indicate that two trials, rather than a single trial, were run for that particular compound in that particular assay.

TABLE A

| | IN-VITRO PLATELET AGGREGATION IN PRP | | |
|---|---|---|---|
| Compound | Dog PRP IC$_{50}$ Micro M | % Inhibition | Test Concentration |
| (±)-cis-6-[4-[4-(aminoiminomethyl)phenyl]butyl]tetrahydro-4-phenyl-2H-pyran-2-one, trifluoroacetate | 4.2 | 100 | 1 × 10$^{-5}$ |
| (±)-cis-6-[4-[4-(aminoiminomethyl)phenyl]butyl]tetrahydro-4-hydroxy-2H-pyran-2-one, trifluoroacetate | 5.3 4.1 | 89 96 | 1 × 10$^{-5}$ 1 × 10$^{-5}$ |
| (±)-trans-6-[4-[4-(aminoiminomethyl)phenyl]butyl]tetrahydro-4-hydroxy-2H-pyran-2-one, trifluoroacetate | | 36 | 1 × 10$^{-5}$ |
| (±)-6-[4-[4-(aminoiminomethyl)phenyl]butyl]tetrahydro-2H-pyran-2-one, trifluoroacetate | | 29 38 | 1 × 10$^{-5}$ 1 × 10$^{-5}$ |
| (±)-cis-6-[4-[4-(aminoiminomethyl)phenyl)butyl]tetrahydro-4-methyl-2H-pyran-2-one, trifluoroacetate | 7.1 | 74 | 1 × 10$^{-5}$ |
| (±)-cis-6-[4-(4-(aminoiminomethyl)phenyl)butyl]-4-ethenyl-tetrahydro-2H-pyran-2-one, trifluoroacetate | 2.6 | 100 | 1 × 10$^{-5}$ |
| (±)-cis-methyl 2-[4-[4-(aminoiminomethyl) | 4.0 | 100 | 1 × 10$^{-5}$ |

TABLE A-continued

IN-VITRO PLATELET AGGREGATION IN PRP

| Compound | Dog PRP IC$_{50}$ Micro M | % Inhibition | Test Concentration |
|---|---|---|---|
| phenyl]butyl]tetrahydro-6-oxo-2H-pyran-4-acetate | | | |
| (±)-cis-6-[4-[4-(aminoiminomethyl)phenyl)butyl]tetrahydro-4-(3-pyridinyl)-2H-pyran-2-one, ditrifluoroacetate | 0.16 | 100 | 1 × 10$^{-5}$ |
| (±)cis-6-[4-(aminoiminomethyl)phenyl]butyl]tetrahydro-4-[(phenylsulfonyl)methyl]-2H-pyran-2-one, trifluoroacetate | 2.6 | 100 | 1 × 10$^{-5}$ |
| (±)-trans-6-[4-[4-(aminoimino)phenyl)butyl]tetrahydro-4-phenyl-2H-pyran-2-one, trifluoroacetate | | 7 | 1 × 10$^{-5}$ |
| N-[4-(aminoiminomethyl)phenyl]tetrahydro-6-oxo-2H-pyran-2-propanamide, trifluoroacetate | 2.9 | | |
| N-[4-(aminomethyl)phenyl]tetrahydro-6-oxo-4S-hydroxy-2H-pyran-2-propanamide, trifluoroacetate | 0.35 | | |

What We claim Is:

1. A compound of the formula

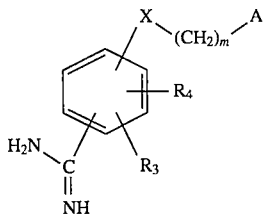

or a pharmaceutically acceptable salt thereof, wherein

R$_3$ and R$_4$ are each independently selected from the group consisting of hydrogen, alkyl having 1 to 6 carbon atoms, hydroxy, alkoxy having 1 to 6 carbon atoms and halo;

X is —CH$_2$CH$_2$—, —CH═CH—, —C≡C— or HNCO m is an integer from 1 to 3; and

A is the group

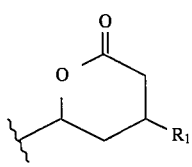

wherein

R$_1$ is a fully unsaturated heteromonocyclic ring structure having 5 or 6 ring carbon atoms wherein one of the ring carbon atoms is replaced by nitrogen, oxygen or sulfur.

2. A compound according to claim 1 which is (±)-cis-6-[4-[4-(aminoiminomethyl)phenyl]butyl]tetrahydro-4(3-pyridinyl)-2H-pyran-2-one, ditrifluoroacetate.

3. A pharmaceutical composition useful for inhibiting platelet aggregation comprising an effective amount of a compound according to claim 1 together with one or more non-toxic pharmaceutically acceptable carriers.

4. A pharmaceutical composition according to claim 3 wherein the compound is (±)-cis-6-[4-[4-(aminoiminomethyl)phenyl]butyl]tetrahydro-4-(3-pyridinyl)-2H-pyran-2-one, ditrifluoroacetate.

5. A method of treating a mammal to inhibit platelet aggregation comprising administering a therapeutically effective dose of a compound of claim 1 to a mammal in need of said treatment.

6. A method according to claim 5 wherein said compound is (±)-cis-6-[4-[4-(aminoiminomethyl)phenyl]butyl]tetrahydro-4-(3-pyridinyl)-2H-pyran-2-one, ditrifluoroacetate.

* * * * *